United States Patent
Nakamura

(10) Patent No.: US 10,564,126 B2
(45) Date of Patent: Feb. 18, 2020

(54) OPTICAL POLARIZATION INSPECTION DEVICE AND METHOD

(71) Applicant: HAMAMATSU PHOTONICS K.K., Hamamatsu-shi, Shizuoka (JP)

(72) Inventor: Tomonori Nakamura, Hamamatsu (JP)

(73) Assignee: HAMAMATSU PHOTONICS K.K., Hamamatsu-shi, Shuzouka (JP)

( * ) Notice: Subject to any disclaimer, the term of this patent is extended or adjusted under 35 U.S.C. 154(b) by 0 days.

(21) Appl. No.: 15/780,293

(22) PCT Filed: Nov. 15, 2016

(86) PCT No.: PCT/JP2016/083855
§ 371 (c)(1),
(2) Date: May 31, 2018

(87) PCT Pub. No.: WO2017/094495
PCT Pub. Date: Jun. 8, 2017

(65) Prior Publication Data
US 2018/0348165 A1   Dec. 6, 2018

(30) Foreign Application Priority Data

Dec. 3, 2015 (JP) .................. 2015-236664

(51) Int. Cl.
*G01N 27/72* (2006.01)
*G01R 31/302* (2006.01)
(Continued)

(52) U.S. Cl.
CPC .......... *G01N 27/72* (2013.01); *G01R 31/302* (2013.01); *G01R 33/0322* (2013.01); *G02B 27/28* (2013.01)

(58) Field of Classification Search
CPC ........ G03H 1/00; G03H 2210/00; G01R 1/00; G01N 1/00; G01N 2201/00; B82Y 5/00;
(Continued)

(56) References Cited

U.S. PATENT DOCUMENTS

| 9,640,449 B2* | 5/2017 | Goodwin | G01N 21/8806 |
| 2013/0148113 A1* | 6/2013 | Oku | G01N 21/8806 356/237.2 |

(Continued)

FOREIGN PATENT DOCUMENTS

| JP | S61-260211 A | 11/1986 |
| JP | H04-279856 A | 10/1992 |

(Continued)

OTHER PUBLICATIONS

International Preliminary Report on Patentability dated Jun. 14, 2018 for PCT/JP2016/083855.

*Primary Examiner* — Huy Q Phan
*Assistant Examiner* — Temilade S Rhodes-Vivour
(74) *Attorney, Agent, or Firm* — Drinker Buddle & Reath LLP

(57) ABSTRACT

An inspection apparatus comprises a light output unit configured to output first light having a first wavelength and second light having a second wavelength, a magneto-optical crystal arranged so that a reflection film faces a measurement target, a light detection unit configured to detect the first light and the second light, and a light guide optical system configured to guide the first light and the second light toward the magneto-optical crystal and the measurement target, and guide the first light reflected by the magneto-optical crystal and the second light reflected by the measurement target toward the light detection unit. The light guide optical system comprises an optical path switching element configured to perform switching between optical paths of a plurality of optical elements so that the first light and the second light are selectively incident on the light detection unit.

10 Claims, 30 Drawing Sheets

(51) Int. Cl.
*G01R 33/032* (2006.01)
*G02B 27/28* (2006.01)

(58) Field of Classification Search
CPC ......... G02F 1/00; G02F 2201/00; G02B 1/00; G02B 2207/00
See application file for complete search history.

(56) References Cited

U.S. PATENT DOCUMENTS

| | | | | |
|---|---|---|---|---|
| 2013/0222909 A1* | 8/2013 | Makikawa | ............... | C30B 13/24 359/484.03 |
| 2014/0225606 A1* | 8/2014 | Endo | ...................... | G01N 27/82 324/260 |
| 2014/0320957 A1* | 10/2014 | Ouchi | ................ | G02B 21/0032 359/388 |
| 2015/0146200 A1* | 5/2015 | Honda | ................. | G01N 21/956 356/237.5 |

FOREIGN PATENT DOCUMENTS

| | | |
|---|---|---|
| JP | H06-27034 A | 2/1994 |
| JP | H07-287059 A | 10/1995 |
| JP | H11-304715 A | 11/1999 |
| JP | 2012-68261 A | 4/2012 |
| JP | 2013-544352 A | 12/2013 |
| JP | 2014-153318 A | 8/2014 |
| JP | 2015-200645 A | 11/2015 |
| WO | WO-2012/049538 A1 | 4/2012 |

\* cited by examiner

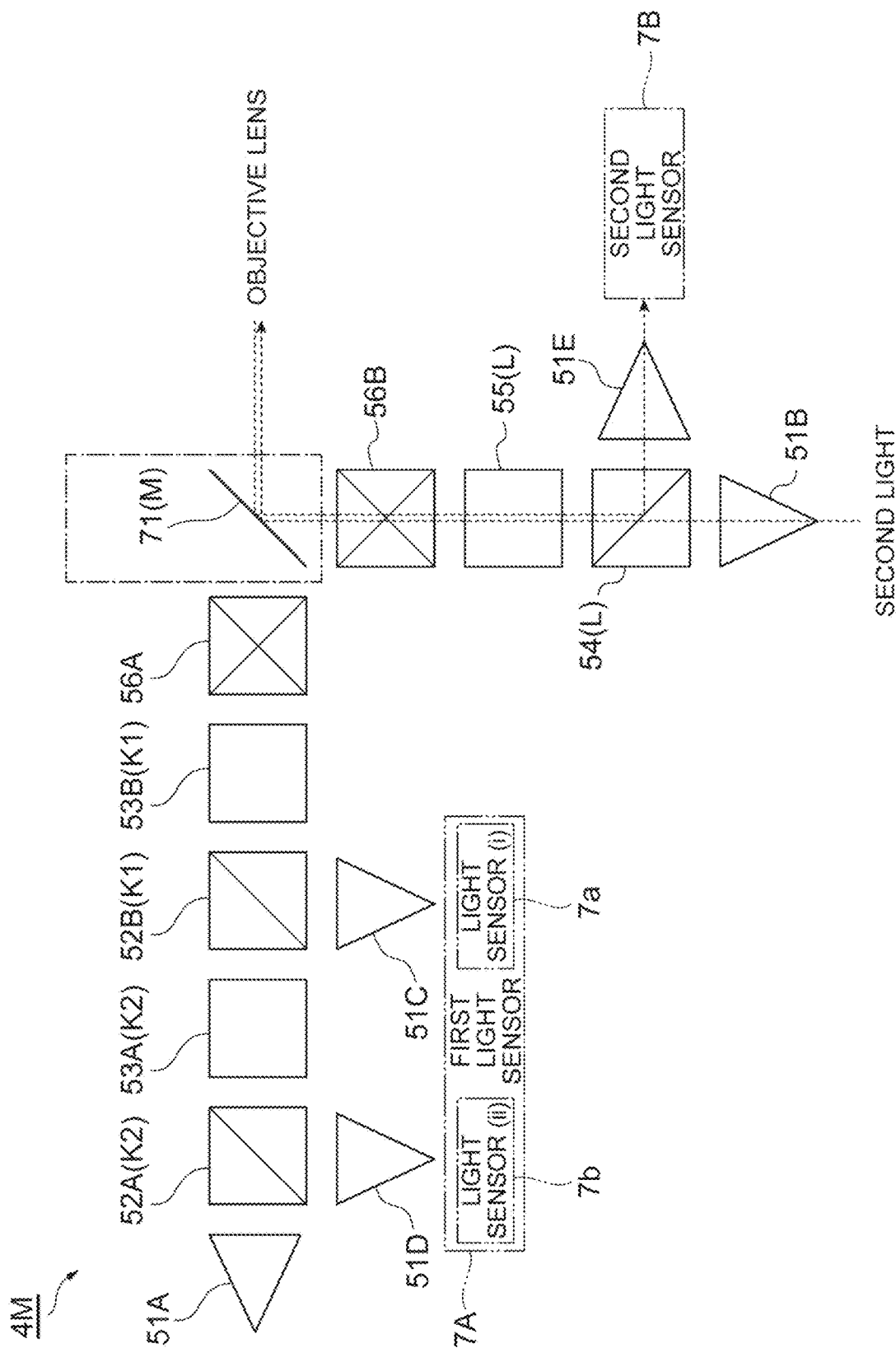

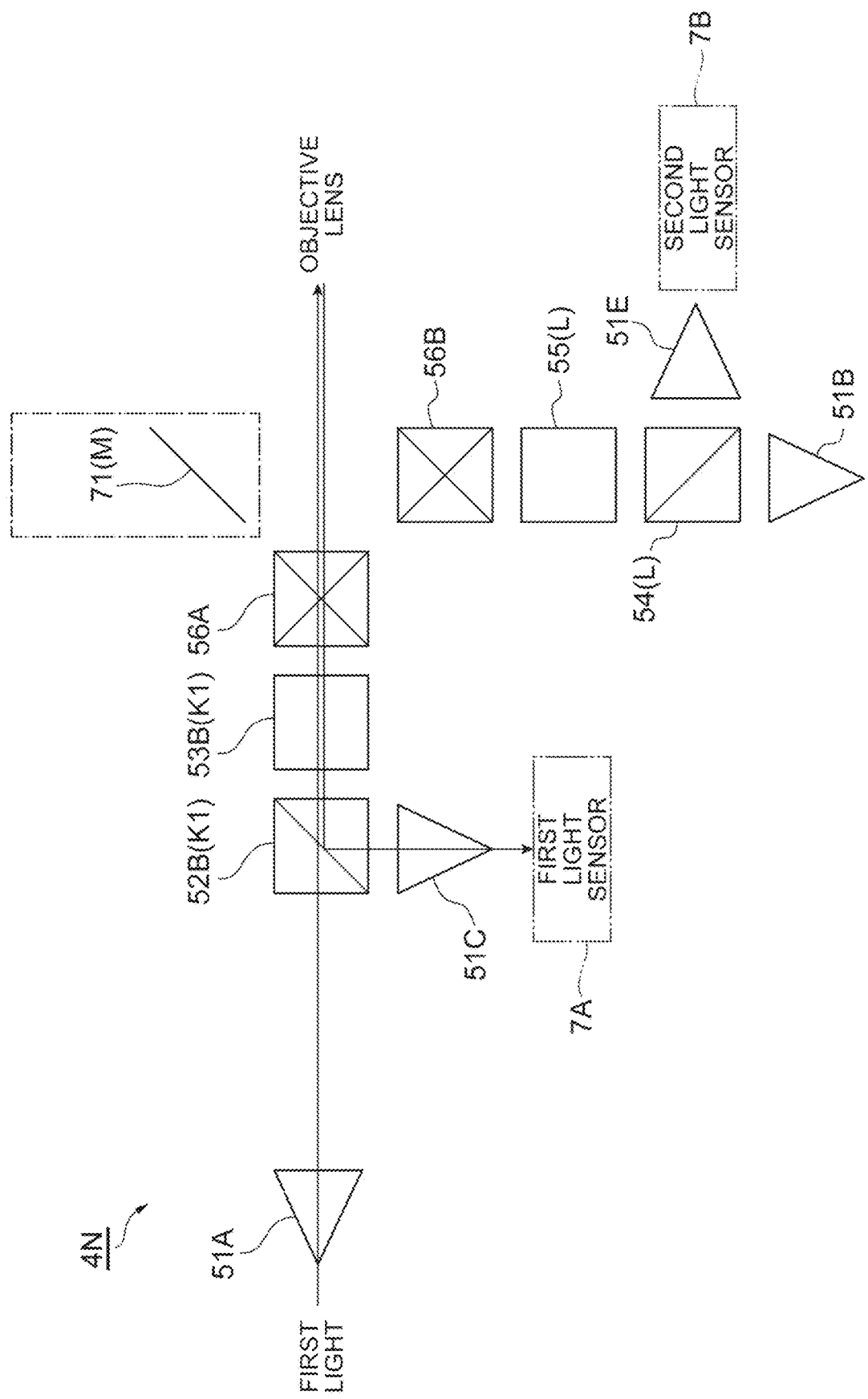

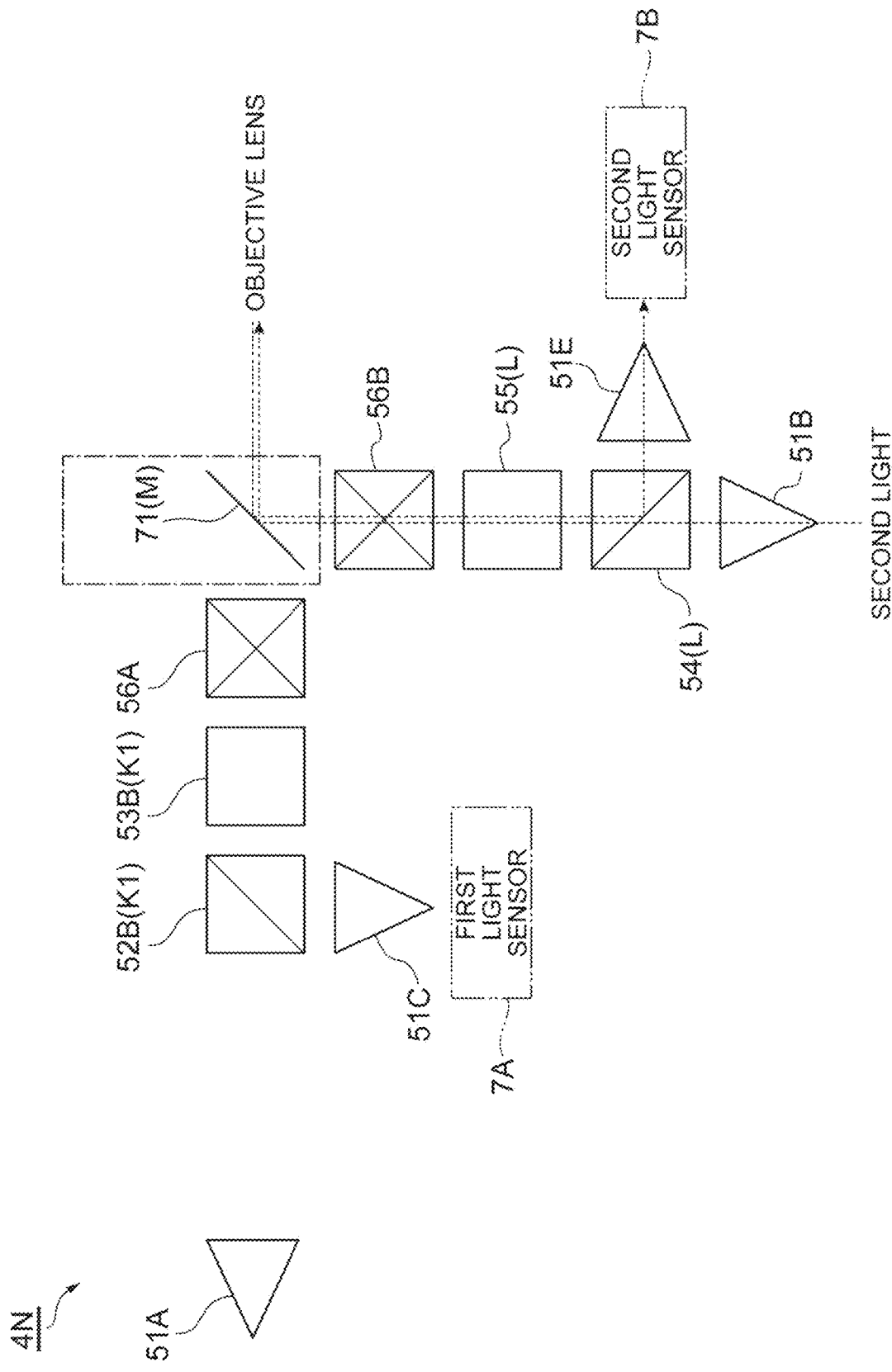

OPTICAL POLARIZATION INSPECTION DEVICE AND METHOD

TECHNICAL FIELD

The present invention relates to an inspection apparatus and an inspection method using light probing technology.

BACKGROUND ART

In light probing technology for inspecting a measurement target such as a semiconductor device, a measurement target is irradiated with light emitted from a light source and measurement light (reflected light) from the measurement target is detected by a light sensor to acquire a detection signal. In a magneto-optical frequency mapping (MOFM) method, which is a type of light probing technology, a magneto-optical crystal is arranged facing a measurement target and reflected light whose polarization state has changed in accordance with a magneto-optical effect of a magneto-optical crystal is detected by a light sensor. In this method, the presence/absence of abnormality of the measurement target is detected on the basis of a distribution of a magnetic field occurring in the measurement target. For example, in Patent Literature 1, a method of arranging a magneto-optical film with respect to a sample, acquiring an image of light obtained by reflecting linearly polarized light radiated to the magneto-optical film by a camera, and mapping a magnetic field of the sample and a flow of an electric current is disclosed.

CITATION LIST

Patent Literature

[Patent Literature 1] Japanese Unexamined Patent Publication No. 2013-544352

SUMMARY OF INVENTION

Technical Problem

In the inspection of a measurement target, a pattern of the measurement target (a circuit pattern or the like) may be acquired by irradiating a measurement target with light emitted from a light source. In this case, for example, by superimposing a distribution of a magnetic field occurring in the measurement target and a pattern of the measurement target, it is easy to ascertain a position where an abnormality has occurred.

Meanwhile, a rotation angle of polarized light with respect to the magnetic field in a magneto-optical crystal generally has wavelength dependence. For example, if a wavelength of incident light is shorter than 1 μm, the rotation angle of the polarized light becomes larger when the wavelength becomes shorter. On the other hand, a wavelength range of light suitable for a desired measurement target may be different from a wavelength range for which the magneto-optical crystal has high sensitivity. For example, if a semiconductor device is used as the measurement target, the wavelength range of light with respect to which silicon has sufficient transparency is an infrared range longer than 1 μm. When a difference between these wavelengths increases, the accuracy of measurement may decrease due to characteristics of an optical element and wavelength dependency of detection sensitivity of a light detection unit. However, if separate optical paths are provided for light having different wavelengths, there is a problem in that a large number of optical elements are required and an apparatus configuration becomes complicated.

The present invention has been made to solve the above problems, and an objective of the present invention is to provide an inspection apparatus and an inspection method capable of accurately performing both detection of the presence/absence of abnormality of a measurement target and acquisition of a pattern while avoiding complication of a configuration.

Solution to Problem

According to an aspect of the present invention, an inspection apparatus for inspecting a measurement target comprises a light output unit configured to output first light having a first wavelength and second light having a second wavelength different from the first wavelength; a magneto-optical crystal having a reflection surface configured to reflect the first light, the reflection surface being arranged facing the measurement target; a light detection unit configured to detect the first light and the second light; and a light guide optical system comprising a plurality of optical elements and configured to guide the first light and the second light toward the magneto-optical crystal and the measurement target and guide the first light reflected by the magneto-optical crystal and the second light reflected by the measurement target toward the light detection unit, wherein the light guide optical system comprises an optical path switching element configured to perform switching between optical paths of the plurality of optical elements so that the first light and the second light are selectively incident on the light detection unit.

In this inspection apparatus, the presence/absence of abnormality of the measurement target can be detected on the basis of a result of detecting the first light reflected by the magneto-optical crystal and the pattern of the measurement target can be acquired on the basis of a result of detecting the second light reflected by the measurement target. The light guide optical system configured to guide the first light and the second light comprises an optical path switching element configured to cause the first light and the second light to be selectively incident on the light detection unit. While optical elements having wavelength dependency suitable for the first wavelength and the second wavelength are used in the light guide optical system, through the optical path switching element, optical elements for forming the optical path of the first light and optical elements for forming the optical path of the second light can be partially shared. Therefore, it is possible to accurately perform both detection of the presence/absence of abnormality of the measurement target and acquisition of the pattern while avoiding complication of a configuration.

Also, the light output unit may comprise a first light source configured to emit the first light and a second light source configured to emit the second light. In this case, it is possible to output the first light and the second light having different wavelengths with sufficient intensities and improve SN ratios of the light sources.

Also, the light detection unit may comprise a first light sensor configured to detect the first light and a second light sensor configured to detect the second light. In this case, it is possible to cause the light detection unit to have sufficient sensitivity with respect to the first light and the second light and accurately perform both detection of the presence/absence of abnormality of a measurement target and acquisition of a pattern.

Also, the light guide optical system may comprise a polarization control element configured to guide one polarized component of the first light to the light detection unit. Thereby, it is possible to suitably detect a change in polarization of the first light in the magneto-optical crystal.

Also, the light guide optical system may further comprise a polarization control element configured to guide the other polarized component of the first light to the light detection unit. In this case, in the light detection unit, differential detection of one polarized component of the first light and the other polarized component of the first light is possible.

Also, the light guide optical system may comprise a polarization control element configured to guide one polarized component of the second light to the light detection unit. Thereby, in the light guide optical system, optical elements for forming the optical path of the first light and optical elements for forming the optical path of the second light can be partially shared to a greater extent.

Also, the optical path switching element may comprise a Faraday rotator and a wavelength plate. In this case, it is possible to configure the optical path switching element with a simple configuration.

Also, the optical path switching element may comprise a dichroic mirror. In this case, it is possible to configure the optical path switching element with a simple configuration.

Also, the optical path switching element may comprise a galvanomirror. In this case, it is possible to configure the optical path switching element with a simple configuration.

Also, the optical path switching element may comprise an optical mirror. In this case, it is possible to configure the optical path switching element with a simple configuration.

Also, the light guide optical system may be configured to comprise a dichroic mirror, and the dichroic mirror may be arranged in a stage previous to the polarization control element. In this case, it is possible to align a polarization direction of light through the polarization control element in a stage subsequent to the dichroic mirror. Therefore, an optical path of the first light and an optical path of the second light may be formed at either a reflection side or a transmission side of the dichroic mirror and a degree of freedom in design of the light guide optical system can be secured.

Also, the measurement target may be a semiconductor device. According to this inspection apparatus, it is possible to accurately perform both detection of the presence/absence of abnormality of a semiconductor device and acquisition of a pattern.

Also, the first wavelength may be shorter than the second wavelength. It is possible to accurately perform both detection of the presence/absence of abnormality of a measurement target and acquisition of a pattern by using a more preferable wavelength with respect to a magneto-optical crystal or a measurement target.

Also, according to an aspect of the present invention, an inspection method of inspecting a measurement target by using a magneto-optical crystal arranged facing the measurement target comprises the step of: guiding first light having a first wavelength and second light having a second wavelength different from the first wavelength toward the magneto-optical crystal and the measurement target through a light guide optical system and detecting the first light and the second light reflected by the magneto-optical crystal or the measurement target, wherein the step comprises the steps of: outputting the first light from a light output unit and detecting the first light in a light detection unit via the light guide optical system; selectively performing switching between optical paths of the light guide optical system so that the second light is incident on the light detection unit; and outputting the second light from the light output unit and detecting the second light in the light detection unit via the light guide optical system.

In this inspection method, for example, the presence/absence of abnormality of a measurement target can be detected on the basis of a result of detecting the first light reflected by the magneto-optical crystal and the pattern of the measurement target can be acquired on the basis of a result of detecting the second light reflected by the measurement target. In the light guide optical system for guiding the first light and the second light, it is possible to accurately perform both detection of the presence/absence of abnormality of a measurement target and acquisition of a pattern by switching an optical path for causing the first light and the second light to be selectively incident on the light detection unit.

Advantageous Effects of Invention

In an inspection apparatus and an inspection method, it is possible to accurately perform both detection of the presence/absence of abnormality of a measurement target and acquisition of a pattern while avoiding complication of a configuration.

BRIEF DESCRIPTION OF DRAWINGS

FIG. 28 is a diagram illustrating an optical path of second light in the light guide optical system in the inspection apparatus according to the thirteenth embodiment.

FIG. 29 is a diagram illustrating an optical path of first light in a light guide optical system in an inspection apparatus according to a fourteenth embodiment.

FIG. 30 is a diagram illustrating an optical path of second light in the light guide optical system in the inspection apparatus according to the fourteenth embodiment.

DESCRIPTION OF EMBODIMENTS

Hereinafter, preferred embodiments of an inspection apparatus and an inspection method according to an aspect of the present invention will be described in detail with reference to the drawings.

First Embodiment

Figure 1:
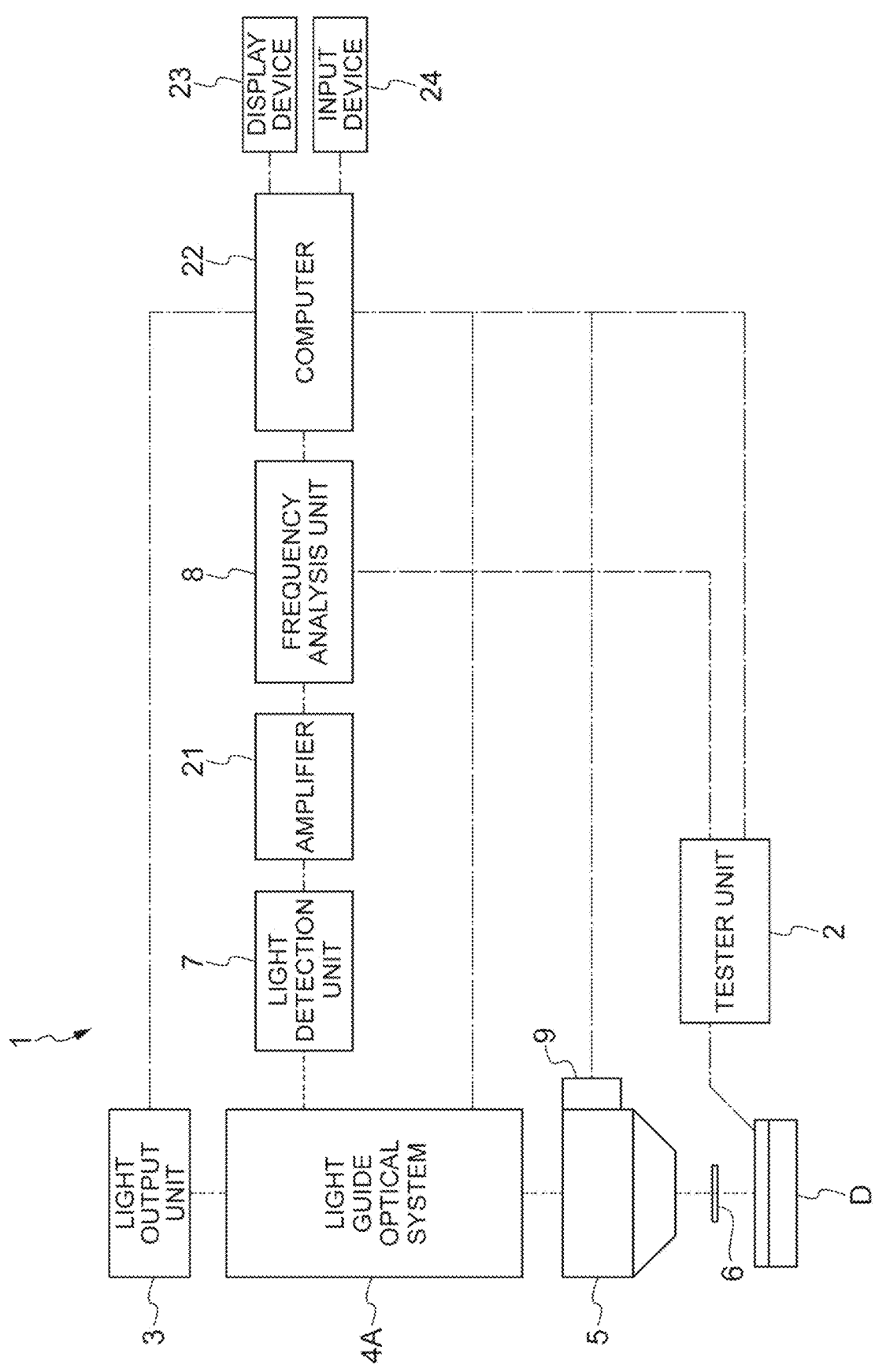
FIG. 1 is a schematic diagram illustrating an inspection apparatus according to a first embodiment.

FIG. 1 is a schematic diagram illustrating an inspection apparatus according to a first embodiment. The inspection apparatus 1 according to the first embodiment is an apparatus configured to inspect a measurement target D. The inspection apparatus 1 includes a tester unit 2, a light output unit 3, a light guide optical system 4A, an objective lens 5, a magneto-optical crystal 6, and a light detection unit 7. The light output unit 3, the light guide optical system 4A, the objective lens 5, the magneto-optical crystal 6, and the light detection unit 7 are optically coupled. In the present embodiment, the measurement target D is, for example, a semiconductor device. Examples of the semiconductor device include an integrated circuit having a PN junction such as a transistor, a large current/high voltage MOS transistor and a bipolar transistor.

The integrated circuit includes, for example, a small scale integration (GSI) circuit, a medium scale integration (MSI) circuit, a large scale integration (LSI) circuit, a very large scale integration (VLSI) circuit, an ultra large scale integration (ULSI) circuit, a giga-scale integration (GSI) circuit, and the like. The measurement target D is not limited to a semiconductor device, and may be an amorphous transistor formed on a glass surface, a polysilicon transistor, or a thin film transistor (TFT) such as an organic transistor.

The measurement target D is electrically connected to the tester unit 2. The tester unit 2 is electrically connected to the frequency analysis unit 8. The tester unit 2 operates by receiving electric power supplied from a power source (not illustrated), and repeatedly applies a modulation current signal to the measurement target D. In the measurement target D, a modulation magnetic field is generated in association with the modulation current signal. An optical signal according to the modulation magnetic field is detected by a light detection unit 7 to be described below, so that measurement light is detected at a specific frequency. Also, the tester unit 2 does not necessarily have to apply a modulation current signal, and may apply a CW current signal for generating pulsed light according to the detection frequency.

The light output unit 3 is a part configured to output first light having a first wavelength and second light having a second wavelength different from the first wavelength. The first light and the second light may be CW light or pulsed light. Also, the first light and the second light may be either incoherent light or coherent light. Examples of light sources that output incoherent light include an SLD, an ASE light sources, an LED, and the like. Examples of a light source configured to output coherent light include a solid laser light source, a semiconductor laser light source, and the like. The light output from the light output unit 3 is incident on the light guide optical system 4A.

In the present embodiment, the wavelength of the first light is a wavelength of 1 μm or less, for which sensitivity in the magneto-optical crystal 6 is sufficiently high. It is preferable that the wavelength of the first light be, for example, a wavelength of 530 nm or less. Also, the wavelength of the second light is a wavelength suitable for the measurement target D. When the measurement target D is a semiconductor device, it is preferable that silicon have sufficient transparency with respect to the wavelength of the second light and this wavelength be a wavelength of 1 μm or more reflected by an internal structure in the semiconductor device.

The light output unit 3 may separately include a first light source configured to output first light and a second light source configured to output second light or may include a single light source. If the light output unit 3 includes separate light sources, the first light is output from the light output unit 3 when the presence/absence of abnormality of the measurement target D is detected and the second light is output from the light output unit 3 when a pattern of the measurement target D is acquired. If the light output unit 3 includes a single light source, for example, a YAG laser is used as a light source, and a second harmonic wave (wavelength 532 nm) is generated from a fundamental wave (a wavelength 1064 nm) through a nonlinear optical crystal. Among these waves, the fundamental wave is used as the second light and the second harmonic wave is selectively used as the first light.

The light guide optical system 4A is a part configured to guide the first light and the second light. The light guide optical system 4A includes a plurality of optical elements. The light guide optical system 4A guides the first light and the second light toward the magneto-optical crystal 6 and the measurement target D. Also, the light guide optical system 4A guides the first light reflected by the reflection film 13 of the magneto-optical crystal 6 (see FIG. 2) and the second light reflected by the back surface of the measurement target D (a surface on a side opposite to the magneto-optical crystal 6) through the inside of the measurement target D toward the light detection unit 7. A detailed configuration of the light guide optical system 4A will be described below.

The objective lens 5 is a part configured to focus the first light guided by the light guide optical system 4A on the magneto-optical crystal 6. The objective lens 5 can be switched between, for example, a low magnification objective lens with, for example, a magnification of ×5 and a high magnification objective lens with, for example, a magnification of ×50, through a turret or the like. For example, a holder for holding the magneto-optical crystal 6 is attached to the objective lens 5. The objective lens 5 is moved in the optical axis direction of the first light and the second light by the objective lens driving unit 9, and the focal position for the magneto-optical crystal 6 is adjusted.

Figure 2:
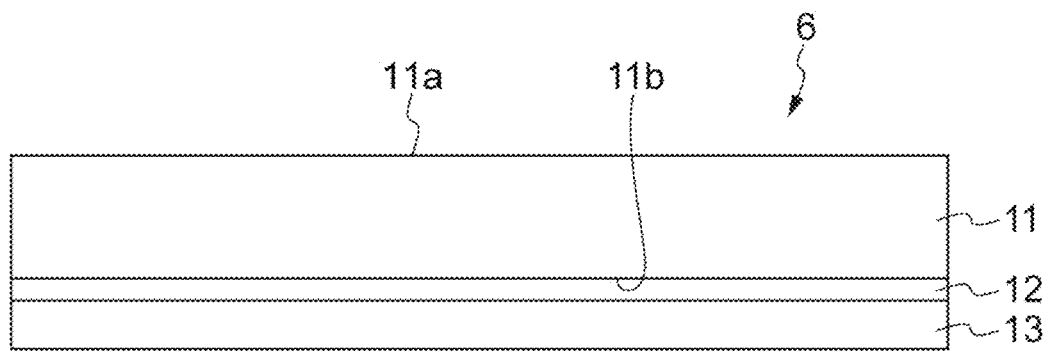
FIG. 2 is a schematic diagram illustrating an example of a magneto-optical crystal.

The magneto-optical crystal 6 is a part configured to change the polarization state of the input light in accordance with the magnetic field generated by the measurement target D due to a magneto optical effect. As illustrated in FIG. 2, the magneto-optical crystal 6 includes a crystal growth substrate 11, a magneto-optical effect layer 12, and a reflection film (a reflection surface) 13. One surface 11a side of the crystal growth substrate 11 serves as an incident surface for the first light and the second light. The magneto-optical effect layer 12 is a thin film including magnetic garnet or the like. Examples of the magnetic garnet include gadolinium gallium garnet (GGG), yttrium iron garnet (YIG), rare-earth iron garnet (RIG), and the like. The magneto-optical effect layer 12 is formed with a thickness of about 1 μm on the other surface 11b side of the crystal growth substrate 11.

The reflection film 13 is, for example, a dielectric multilayer film. The reflection film 13 is provided on a surface of the magneto-optical effect layer 12 opposite to the crystal growth substrate 11. The reflection film 13 has optical characteristics of reflecting the first light and transmitting the second light. As illustrated in FIG. 1, the magneto-optical crystal 6 is arranged facing the measurement target D so that the reflection film 13 side is directed to the measurement target D side. The first light from the one surface 11a side of the crystal growth substrate 11 is incident on the magneto-optical crystal 6, reflected by the reflection film 13, and incident on the light guide optical system 4A again. The second light is transmitted through the magneto-optical crystal 6, reflected by the back surface of the measurement target D through the inside of the measurement target D, transmitted through the magneto-optical crystal 6 again, and incident on the light guide optical system 4A.

The light detection unit 7 is a part configured to detect the first light and the second light. Examples of a light sensor constituting the light detection unit 7 include a photodiode, an avalanche photodiode, a photomultiplier tube, an area image sensor, and the like. The light detection unit 7 may separately include a first light sensor sensitive to the first light and a second light sensor sensitive to the second light. Also, the light detection unit 7 may include a single light sensor having sensitivity to both the first light and the second light.

A detection signal output from the light detection unit 7 is amplified by the amplifier 21 and input to the frequency analysis unit 8 as an amplified signal. The frequency analysis unit 8 is a part configured to extract a measurement frequency component from the amplified signal and output the extracted signal as an analysis signal. As the frequency analysis unit 8, for example, a lock-in amplifier, a spectrum analyzer, a digitizer, a cross domain analyzer (registered trademark), a network analyzer, and the like are used. For example, a measurement frequency is set by the tester unit 2 on the basis of a modulation frequency of a modulation current signal applied to the measurement target D. The frequency analysis unit 8 may output a phase signal indicating a phase difference between the modulation current signal output from the tester unit 2 and the detection signal or the analysis signal.

The analysis signal output by the frequency analysis unit 8 is input to a computer 22. The computer 22 includes a processor, a memory, and the like. A display device 23 such as a monitor and input devices 24 such as a keyboard and a mouse are connected to the computer 22. The computer 22 executes a function of controlling the tester unit 2, the light output unit 3, the light guide optical system 4A, the objective lens driving unit 9, the light detection unit 7, the frequency analysis unit 8 and the like and executes functions such as creation of a magnetic distribution image (a magnetic intensity image and a magnetic phase image), magnetic frequency mapping, creation of an electric current image indicating a current path/current direction based on a magnetic distribution, and creation of a pattern image such as a circuit pattern in the measurement target D on the basis of the analysis signal or the phase signal input from the frequency analysis unit 8. The computer 22 executes each of these functions through a processor.

By scanning irradiation positions of the first light and the second light with respect to the magneto-optical crystal 6 and the measurement target D, a magnetic intensity image indicating a two-dimensional magnetic field intensity distribution and a pattern image in the measurement target D are obtained. By displaying these images on the display device 23, it is possible to perform detection of the presence/absence of abnormality and identification of an abnormal portion in the measurement target D. If the frequency characteristics of the magnetic field are detected at a predetermined position, it is only necessary to execute the magnetic frequency mapping by switching a measurement frequency. Also, similar identification may be performed by displaying the magnetic phase image, the electric current image, or the like created by the computer 22 on the display device 23. Also, if the high-resolution magnetic intensity image and the pattern image are obtained, it is only necessary to execute the process by reducing diameters and scanning ranges of the first light and the second light.

Also, if no lock-in detection is performed, it is not necessary to output a signal of a specific frequency component and it is only necessary to output the amplified signal from the amplifier 21 as it is as the analysis signal from the frequency analysis unit 8. The magnetic distribution image, the electric current image, and the pattern image may be superimposed and displayed on the display device 23.

Next, a configuration of the light guide optical system 4A described above will be described in more detail with reference to FIGS. 3 and 4.

Figure 3:
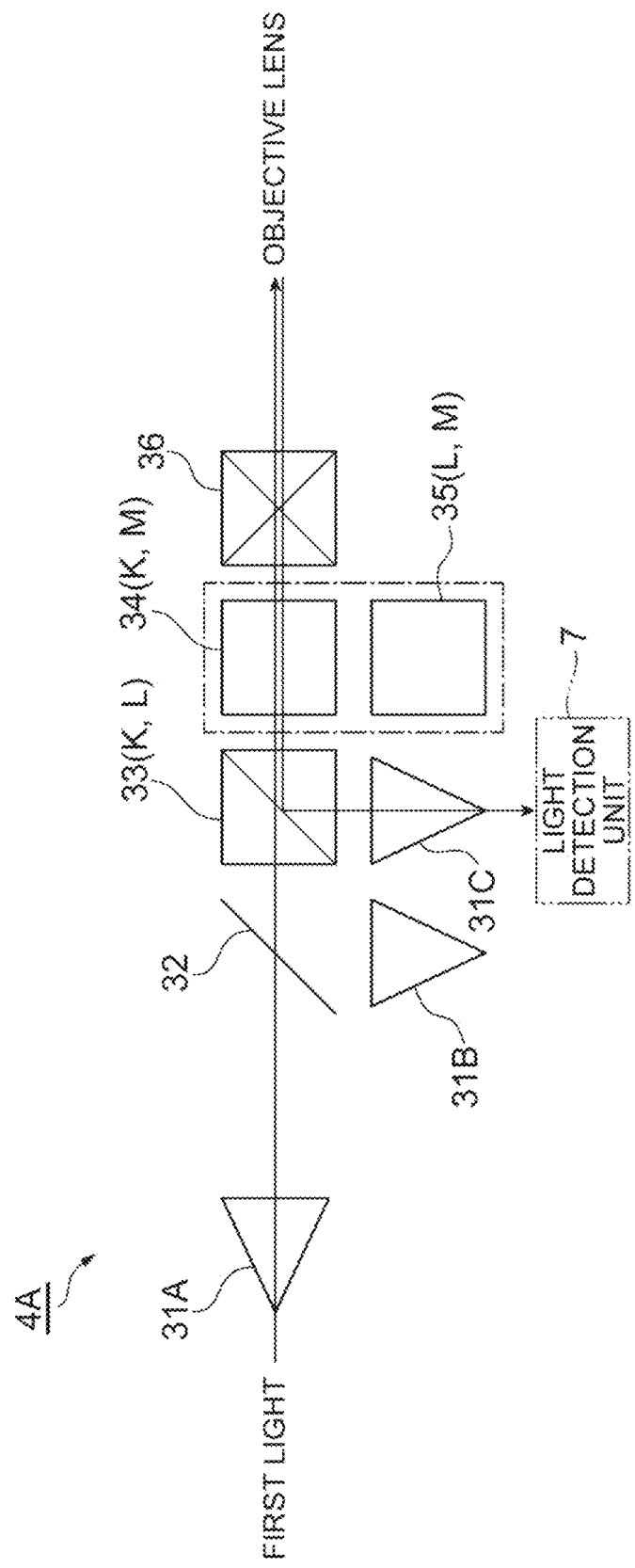
FIG. 3 is a diagram illustrating an optical path of first light in a light guide optical system in the inspection apparatus illustrated in FIG. 1.

As illustrated in FIG. 3, the light guide optical system 4A includes collimators 31A to 31C, a dichroic mirror 32, a polarizing beam splitter 33, a Faraday rotator 34, a λ/4 wavelength plate 35, and a galvanomirror 36 as a plurality of optical elements. The plurality of optical elements are optically coupled. The polarizing beam splitter 33 and the Faraday rotator 34 constitute a polarization control element K configured to guide one polarized component of the first light to the light detection unit 7. The polarizing beam splitter 33 and the λ/4 wavelength plate 35 constitute a polarization control element L configured to guide one polarized component of the second light to the light detection unit 7.

The Faraday rotator 34 and the λ/4 wavelength plate 35 constitute an optical path switching element M configured to perform switching between optical paths through the optical elements so that the first light and the second light are selectively incident on the light detection unit 7. For example, one of the Faraday rotator 34 and the λ/4 wavelength plate 35 is advanced to the optical path through a driving means such as a cylinder and the other is retracted from the optical path. Also, the dichroic mirror 32 is arranged in a stage previous to the polarization control element K in the optical path of the light guide optical system 4A.

In the present embodiment, the dichroic mirror 32 transmits the first light and reflects the second light at substantially a right angle. The polarizing beam splitter 33 transmits light having a polarized component of 0° in a polarization plane and reflects light having a polarized component of 90° in a polarization plane. The Faraday rotator 34 rotates the polarization plane of the input light by 22.5°.

A method of inspecting the measurement target D by using the inspection apparatus 1 includes the step of: guiding first light having a first wavelength and second light having a second wavelength different from the first wavelength toward the magneto-optical crystal 6 and the measurement target D through the light guide optical system 4A and detecting the first light or the second light reflected by the magneto-optical crystal 6 or the measurement target D. In more detail, the step includes the steps of: outputting the first light from the light output unit 3 and detecting the first light in the light detection unit 7 via the light guide optical system 4A; selectively performing switching between optical paths of the light guide optical system 4A so that the second light is incident on the light detection unit 7; and outputting the second light from the light output unit 3 and detecting the second light in the light detection unit 7 via the light guide optical system 4A.

If the first light is output from the light output unit 3, the Faraday rotator 34 is advanced to the optical path of the light guide optical system 4A in the optical path switching element M as illustrated in FIG. 3. The first light is light linearly polarized by 0° in an initial state. The first light is collimated by the collimator 31A, transmitted through the dichroic mirror 32, and incident on the polarizing beam splitter 33. The first light is transmitted through the polarizing beam splitter 33 and guided to the objective lens 5 in a state in which the polarization plane is rotated by 22.5° by the Faraday rotator 34. A position at which the first light is incident on the objective lens 5, i.e., a position at which the first light is incident on the magneto-optical crystal 6, is scanned by the galvanomirror 36.

The polarization plane of the first light reflected by the reflection film 13 of the magneto optical crystal 6 is rotated by α° in accordance with a magneto-optical effect (a Kerr effect, a Faraday effect, and the like) according to a magnetic field (a magnetic field intensity) generated in the measurement target D and incident on the light guide optical system 4A through the objective lens 5 again. The polarization plane of the first light is further rotated by 22.5° by the Faraday rotator 34. Only a polarized component of 90° in the first light whose polarization plane is rotated by 45+α° in total by reciprocating in the Faraday rotator 34 is reflected by the polarizing beam splitter 33 and output to the light detection unit 7 in a state in which the first light is focused by the collimator 31C. The light detection unit 7 detects intensity modulation caused by the rotation of the polarization plane by α° in accordance with the magneto-optical effect.

Figure 4:
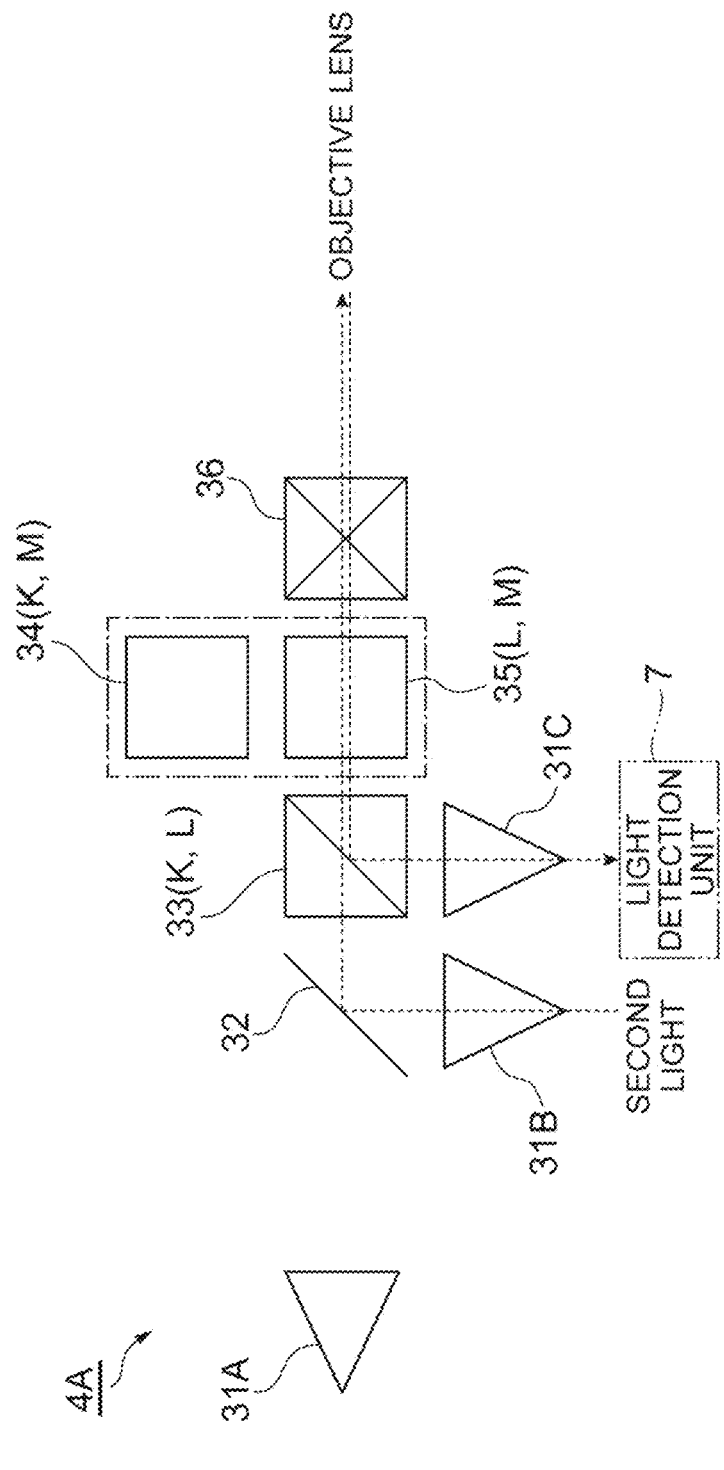
FIG. 4 is a diagram illustrating an optical path of second light in the light guide optical system in the inspection apparatus illustrated in FIG. 1.

When the second light is output from the light output unit 3, the λ/4 wavelength plate 35 is advanced to the optical path of the light guide optical system 4A in the optical path switching element M as illustrated in FIG. 4. The second light is light linearly polarized by 0° in an initial state. The second light is collimated by the collimator 31B, reflected by the dichroic mirror 32, and is incident on the polarizing beam splitter 33. The second light is transmitted through the polarizing beam splitter 33 and is guided to the objective lens 5 in a state in which light is circularly polarized by the λ/4 wavelength plate 35. A position at which the second light is incident on the objective lens 5, i.e., a position at which the second light is incident on the measurement target D, is scanned by the galvanomirror 36.

The second light reflected through the inside of the measurement target D is incident on the light guide optical system 4A through the objective lens 5 again. The second light reciprocates in the λ/4 wavelength plate 35 and hence is linearly polarized light whose polarization plane is rotated by 90° and is reflected by the polarizing beam splitter 33, and output to the light detection unit 7 in a state in which the second light is focused by the collimator 31C.

As described above, in the inspection apparatus 1, the presence/absence of abnormality of the measurement target D can be detected on the basis of a result of detecting the first light reflected by the reflection film 13 of the magneto-optical crystal 6 and the circuit pattern of the measurement target D or the like can be acquired on the basis of a result of detecting the second light reflected by the measurement target D through the inside of the measurement target D. The light guide optical system 4A configured to guide the first light and the second light has an optical path switching element M configured to cause the first light and the second light to be selectively incident on the light detection unit 7. While optical elements having wavelength dependency suitable for the first wavelength and the second wavelength are used in the light guide optical system 4A through the optical path switching element M, optical elements for forming the optical path of the first light and optical elements for forming the optical path of the second light can be partially shared. Therefore, it is possible to accurately perform both detection of the presence/absence of abnormality of the measurement target D and acquisition of a pattern while avoiding complication of a configuration.

In the present embodiment, the dichroic mirror 32, the polarizing beam splitter 33, the galvanomirror 36, and the collimator 31C among the optical elements constituting the light guide optical system 4A can be shared between the optical path of the first light and the optical path of the second light. Also, in the present embodiment, it is preferable that the light output unit 3 include a first light source configured to emit the first light and a second light source configured to emit the second light. In this case, it is possible to output the first light and the second light having different wavelengths with sufficient intensities and improve an SN ratio of the measurement result.

Also, if a single light sensor is used, the sensitivity to the first light and the sensitivity to the second light may be different according to wavelength dependence. In this case, it is preferable to use a light sensor having a characteristic in which priority is given to the sensitivity to the first light and the sensitivity to the first light is higher than the sensitivity to the second light. Also, in the inspection apparatus 1, the optical path switching element M includes the Faraday rotator 34 and the λ/4 wavelength plate 35. In this case, the optical path switching element M can be configured with a simple configuration.

Second Embodiment

An inspection apparatus according to a second embodiment separately includes a first light sensor 7A configured to detect the first light and a second light sensor 7B configured to detect the second light in a light detection unit 7. Also, in association with this, a configuration of a light guide optical system 4B is different from that of the first embodiment. More specifically, in the light guide optical system 4B, a dichroic mirror 41 and a collimator 31D are further arranged in a stage subsequent to the optical path in addition to the configuration of the light guide optical system 4A as illustrated in FIG. 5.

Figure 5:
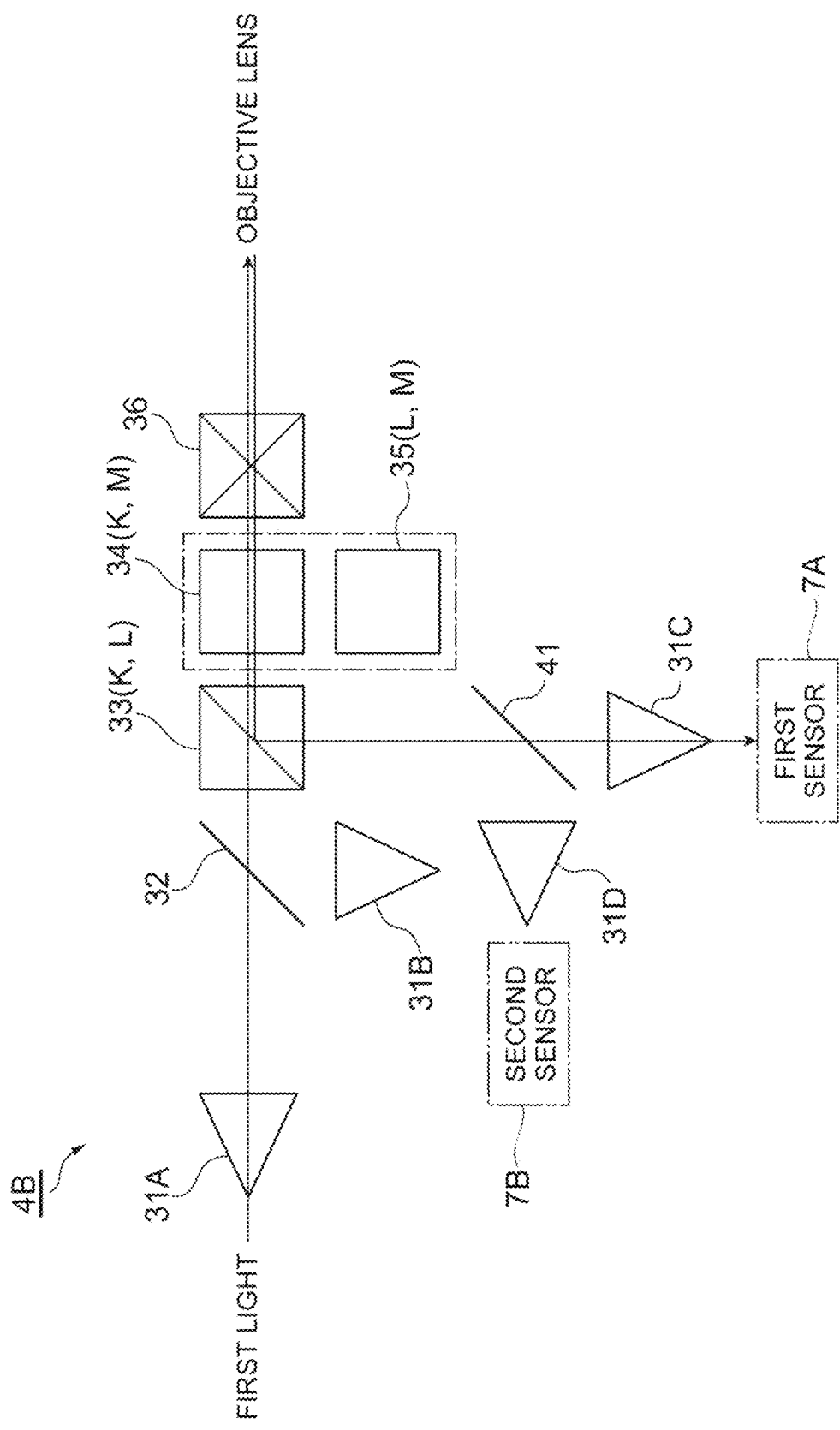
FIG. 5 is a diagram illustrating an optical path of first light in a light guide optical system in an inspection apparatus according to a second embodiment.

As illustrated in FIG. 5, an optical path of first light is similar to that in the first embodiment until the first light is reflected by a reflection film 13 of a magneto-optical crystal 6 and reflected by a polarizing beam splitter 33. The first light reflected by the polarizing beam splitter 33 is transmitted through the dichroic mirror 41 and output to the first light sensor 7A of the light detection unit 7 in a state in which the first light is focused by a collimator 31C.

Figure 6:
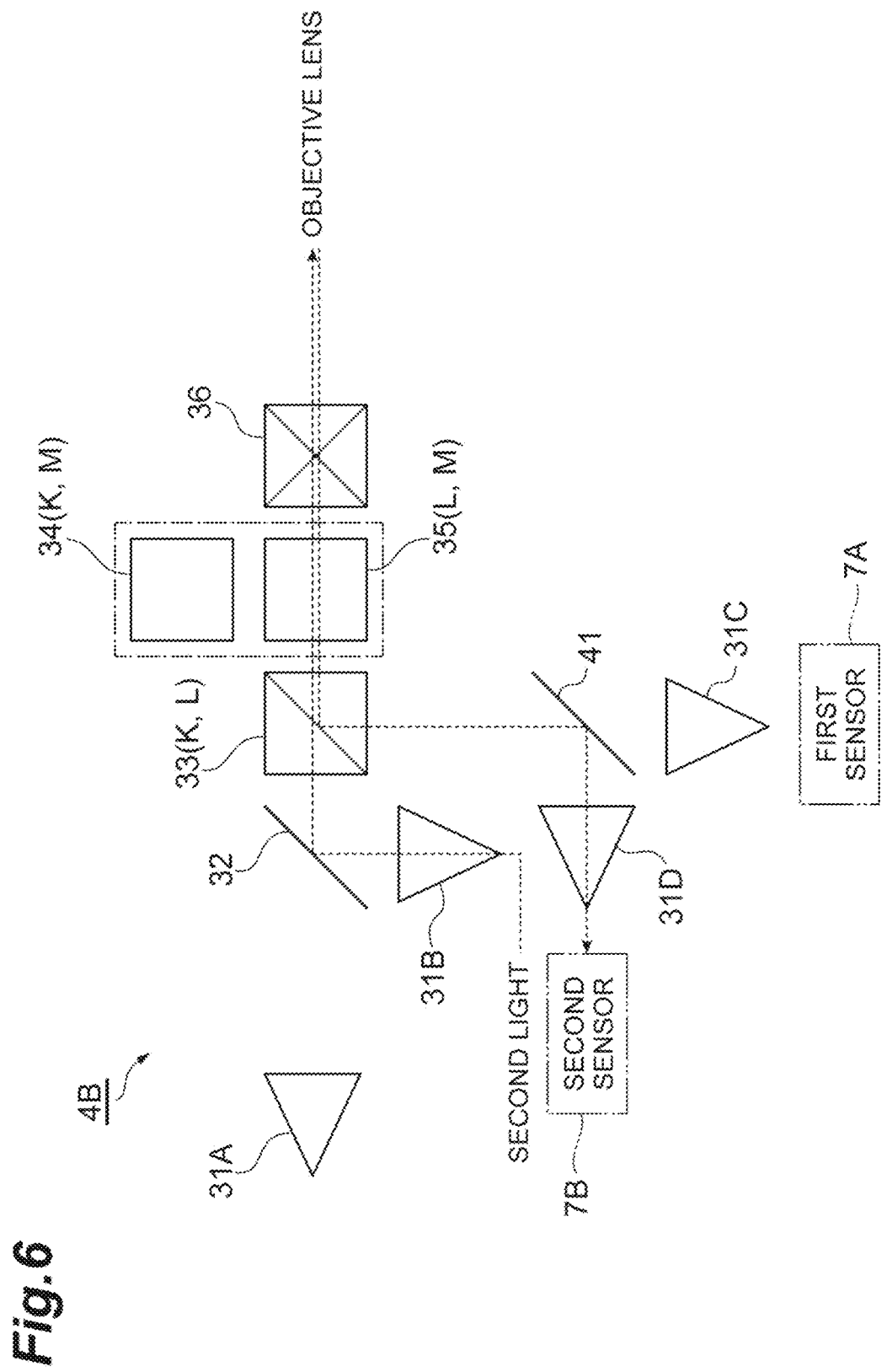
FIG. 6 is a diagram illustrating an optical path of second light in the light guide optical system in the inspection apparatus according to the second embodiment.

As illustrated in FIG. 6, an optical path of second light is similar to that in the first embodiment until the second light is reflected by a measurement target D and reflected by the polarizing beam splitter 33. The second light reflected by the polarizing beam splitter 33 is reflected by the dichroic mirror 41 and output to the second light sensor 7B of the light detection unit 7 in a state in which the second light is focused by the collimator 31D.

Also, in such a form, as in the above-described embodiment, while optical elements having wavelength dependency suitable for a first wavelength and a second wavelength are used in the light guide optical system 4B through an optical path switching element M, optical elements for forming the optical path of the first light and optical elements for forming the optical path of the second light can be partially shared. Therefore, it is possible to accurately perform both detection of the presence/absence of abnormality of the measurement target D and acquisition of a pattern while avoiding complication of a configuration.

Also, in the present embodiment, the light detection unit 7 includes the first light sensor 7A configured to detect the first light and the second light sensor 7B configured to detect the second light. In this case, by arranging the first light sensor 7A having high sensitivity to the first light and the second light sensor 7B having high sensitivity to the second light, it is possible to accurately perform detection of the presence/absence of abnormality of the measurement target and acquisition of a pattern.

Furthermore, in the present embodiment, the dichroic mirror 41 is arranged in a stage previous to polarization control elements K and L. Thereby, a polarization direction of light can be aligned by the polarization control elements K and L in a stage subsequent to the dichroic mirror 41. Therefore, the optical path of the first light and the optical path of the second light may be formed on either the reflection side or the transmission side of the dichroic mirror 41, so that a degree of freedom in design of the light guide optical system 4B can be secured.

Also, in the present embodiment, instead of the dichroic mirror 41 and the collimators 31C and 31D, a single collimator and an optical coupler may be arranged. By using an optical fiber configured to split an output for each wavelength, it is possible to implement a configuration equivalent to the above-described embodiment. It is preferable to use a polarization-maintaining single-mode optical coupler as the optical coupler and it is preferable to use a polarization-maintaining single-mode optical fiber as the optical fiber.

Third Embodiment

An inspection apparatus according to a third embodiment is different from that according to the above-described embodiment in that an optical path switching element M includes a galvanomirror 56 and a first light sensor 7A of a light detection unit 7 includes a light sensor (i) 7a and a light sensor (ii) 7b independent of each other in a light guide optical system 4C. The inspection apparatus according to the third embodiment is different from that according to the first embodiment in that a polarization control element K1 configured to guide one polarized component of first light to the light sensor (i) 7a of the light detection unit 7 and a polarization control element K2 configured to guide the other polarized component of the first light to the light sensor (ii) 7b of the light detection unit 7 are arranged in the light guide optical system 4C.

More specifically, the light guide optical system 4C includes collimators 51A to 51E, polarizing beam splitters 52A and 52B for a visible range, Faraday rotators 53A and 53B, a polarizing beam splitter 54 for a near-infrared range, a λ/4 wavelength plate 55, and the galvanomirror 56 as a plurality of optical elements.

The polarizing beam splitter 52B and the Faraday rotator 53B constitute the polarization control element K1 configured to guide one polarized component of the first light to the light detection unit 7. The polarizing beam splitter 52A and the Faraday rotator 53A constitute the polarization control element K2 configured to guide the other polarized component of the first light to the light detection unit 7. The polarizing beam splitter 54 and the λ/4 wavelength plate 55 constitute a polarization control element L configured to guide one polarized component of the second light to the light detection unit 7.

The galvanomirror 56 functions as the optical path switching element M by adding a first offset or a second offset to a central angle of a scanning range. In the present embodiment, for example, the scanning range of the galvanomirror 56 is +3°, the first offset is +10°, and the second offset is −10°. The galvanomirror 56 rotates in a range of +10°±3° if the first light is output from the light output unit 3 and operates in a range of −10°±3° if the second light is output from the light output unit 3.

The Faraday rotator 53A rotates the polarization plane of the input light by 45°. Also, the Faraday rotator 53B rotates the polarization plane of the input light by 22.5°. The polarizing beam splitter 52A transmits light having a polarized component of 0° in a polarization plane, and reflects light having a polarized component of 90° in a polarization plane. The polarizing beam splitter 52B transmits light having a polarized component of 45° in a polarization plane and reflects light having a polarized component of 135° in a polarization plane.

Figure 7:
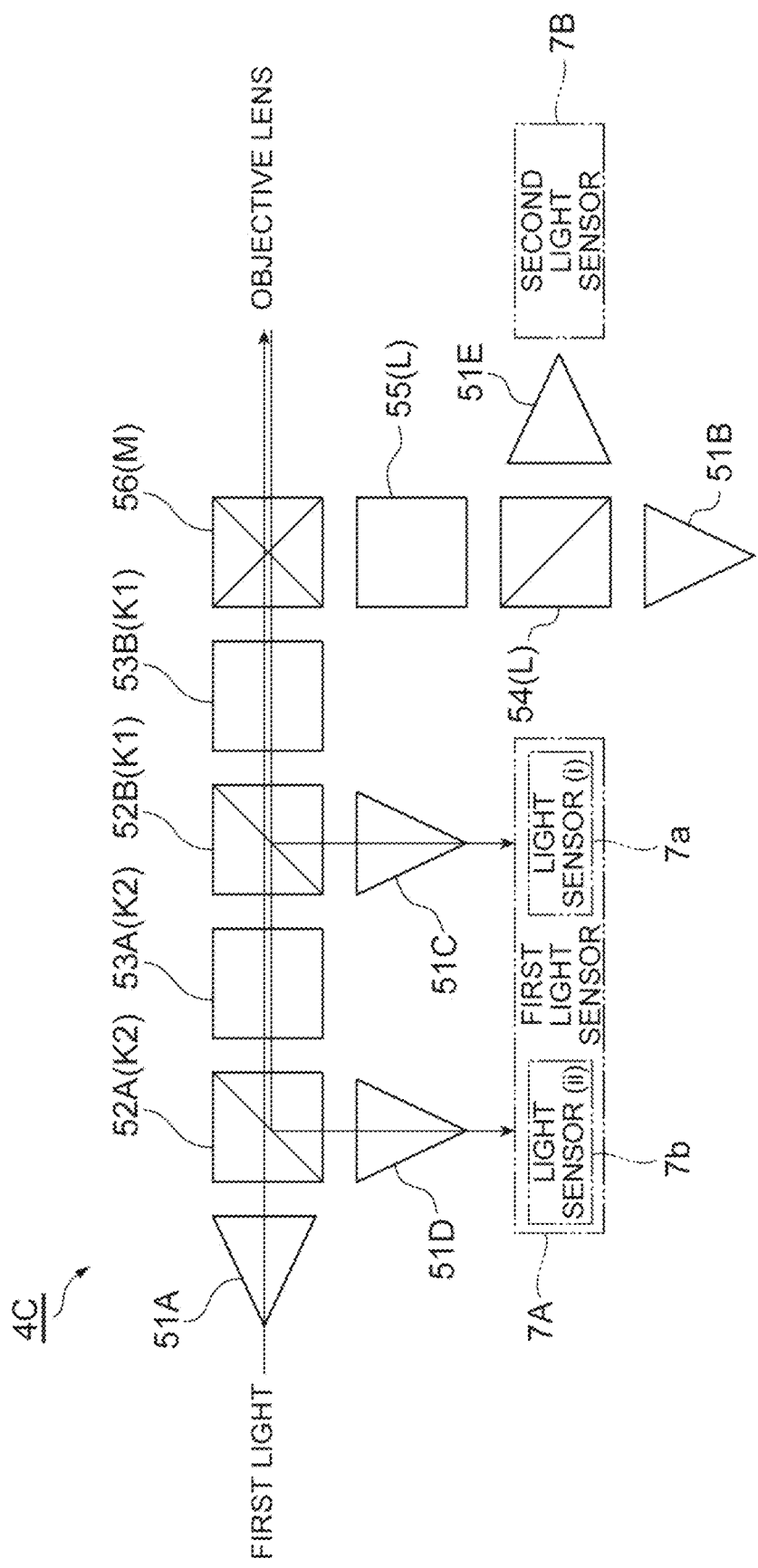
FIG. 7 is a diagram illustrating an optical path of first light in a light guide optical system in an inspection apparatus according to a third embodiment.

If the first light is output from the light output unit 3, a first offset is given to the galvanomirror 56 in the optical path switching element M. The first light is light linearly polarized by 0° in an initial state. As illustrated in FIG. 7, the first light is collimated by the collimator 51A and transmitted through the polarizing beam splitter 52A, and the polarization plane is rotated by 45° by the Faraday rotator 53A. Also, the first light is transmitted through the polarizing beam splitter 52B and further guided to the objective lens 5 after the polarization plane is further rotated by 22.5° by the Faraday rotator 53B. A position at which the first light is incident on the objective lens 5, i.e., a position in which the first light is incident on the magneto-optical crystal 6, is scanned by the galvanomirror 56.

The polarization plane of the first light reflected by the reflection film 13 of the magneto-optical crystal 6 is rotated by $\alpha'$ in accordance with a magneto-optical effect (a Kerr effect, a Faraday effect, and the like) according to a magnetic field (a magnetic field intensity) generated in a measurement target D and incident on the light guide optical system 4C through the objective lens 5 again. The polarization plane of the first light is further rotated by 22.5° by the Faraday rotator 53B. Only a polarized component of 135° in the first light whose polarization plane is rotated by 90+$\alpha$° in total at a point in time at which the first light reciprocates in the Faraday rotator 53B is reflected by the polarizing beam splitter 52B and output to a light sensor (i) 7a of the first light sensor 7A of the light detection unit 7 in a state in which the first light is focused by the collimator 51C.

Also, a polarization plane of the polarized component transmitted through the polarizing beam splitter 52B in the first light is further rotated by 45° by the Faraday rotator 53A and the polarized component is reflected by the polarizing beam splitter 52A and then output to the light sensor (ii) 7b of the first light sensor 7A of the light detection unit 7 in a state in which the first light is focused by the collimator 51D. In the light detection unit 7, differential detection of the light input to the first light sensor 7A is performed. The first light sensor 7A detects intensity modulation caused by the rotation of the polarization plane by $\alpha$° in accordance with the magneto-optical effect. Also, instead of having an independent light sensor, a light sensor configured to have a plurality of light receiving surfaces may be used as the light sensor 7A.

Figure 8:
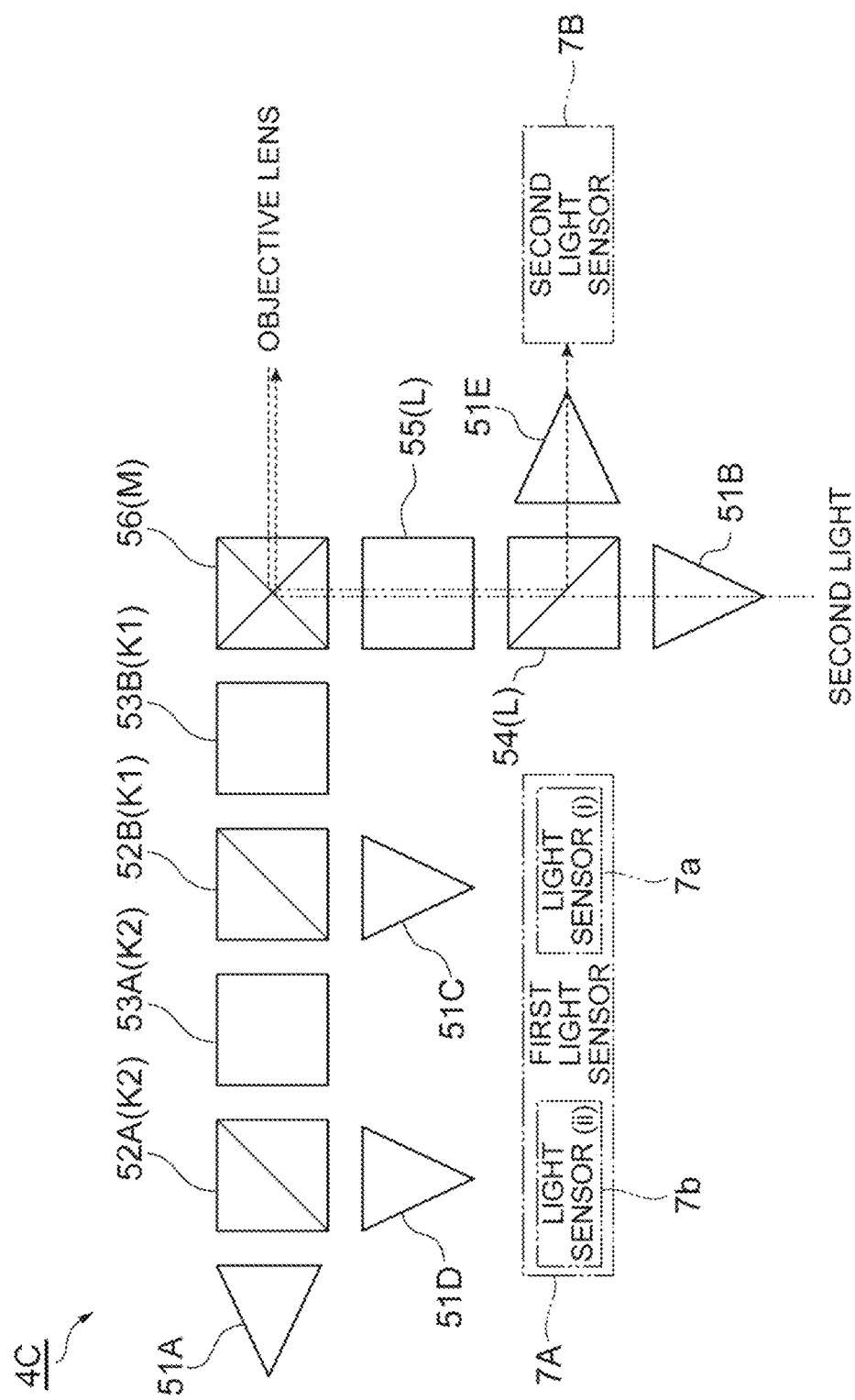
FIG. 8 is a diagram illustrating an optical path of second light in the light guide optical system in the inspection apparatus according to the third embodiment.

If the second light is output from the light output unit 3, a second offset is given to the galvanomirror 56 in the optical path switching element M. The second light is light linearly polarized by 0° in an initial state. As illustrated in FIG. 8, the second light is guided to the objective lens 5 in a state in which the second light is collimated by the collimator 51E, transmitted through the polarizing beam splitter 54, and circularly polarized by the $\lambda$/4 wavelength plate 55. A position at which the second light is incident on the objective lens 5, i.e., a position at which the second light is incident on the measurement target D, is scanned by the galvanomirror 56.

The second light reflected through the inside of the measurement target D is incident on the light guide optical system 4C through the objective lens 5 again. The second light reciprocates in the $\lambda$/4 wavelength plate 55, is linearly polarized light whose polarization plane is rotated by 90°, and is reflected by the polarizing beam splitter 54, and is output to the second light sensor 7B of the light detection unit 7 in a state in which the second light is focused by the collimator 51E.

Also, in such a form, as in the above-described embodiment, while optical elements having wavelength dependency suitable for a first wavelength and a second wavelength are used in the light guide optical system 4C through the optical path switching element M, optical elements for forming an optical path of the first light and optical elements for forming an optical path of the second light can be partially shared. Therefore, it is possible to accurately perform both detection of the presence/absence of abnormality of the measurement target D and acquisition of a pattern while avoiding complication of a configuration. Also, because the optical path switching element M includes only the galvanomirror 56, the optical path switching element M can be simply configured.

In the present embodiment, the galvanomirror 56 among the optical elements constituting the light guide optical system 4C can be shared between the optical path of the first light and the optical path of the second light. Also, in the light detection unit 7, differential detection of one polarized component of the first light and the other polarized component of the first light can be performed. Therefore, even when an SN ratio of a light source is relatively low, it is possible to accurately detect the presence/absence of abnormality of the measurement target D.

Also, in the present embodiment, instead of the polarizing beam splitter 54 and the collimators 51B and 51E, a single collimator and an optical fiber having an optical coupler for dividing the light into orthogonal polarized components may be arranged. By using an optical fiber configured to split the output of each polarized component, it is possible to implement a configuration equivalent to that of the above-described embodiment. As the optical fiber, it is preferable to use a polarization-maintaining single-mode optical fiber.

Fourth Embodiment

Figure 9:
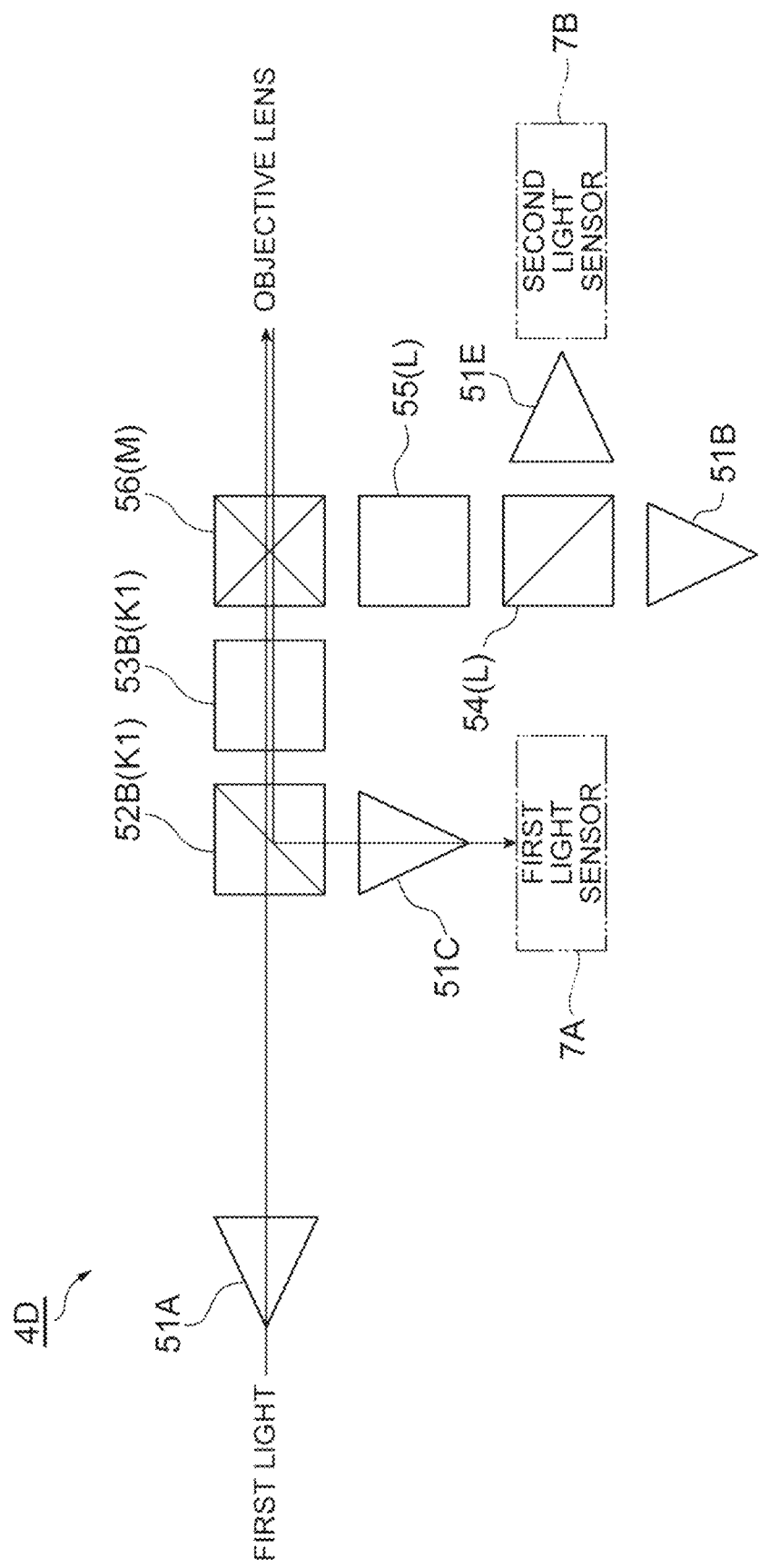
FIG. 9 is a diagram illustrating an optical path of first light in a light guide optical system in an inspection apparatus according to a fourth embodiment.
Figure 10:
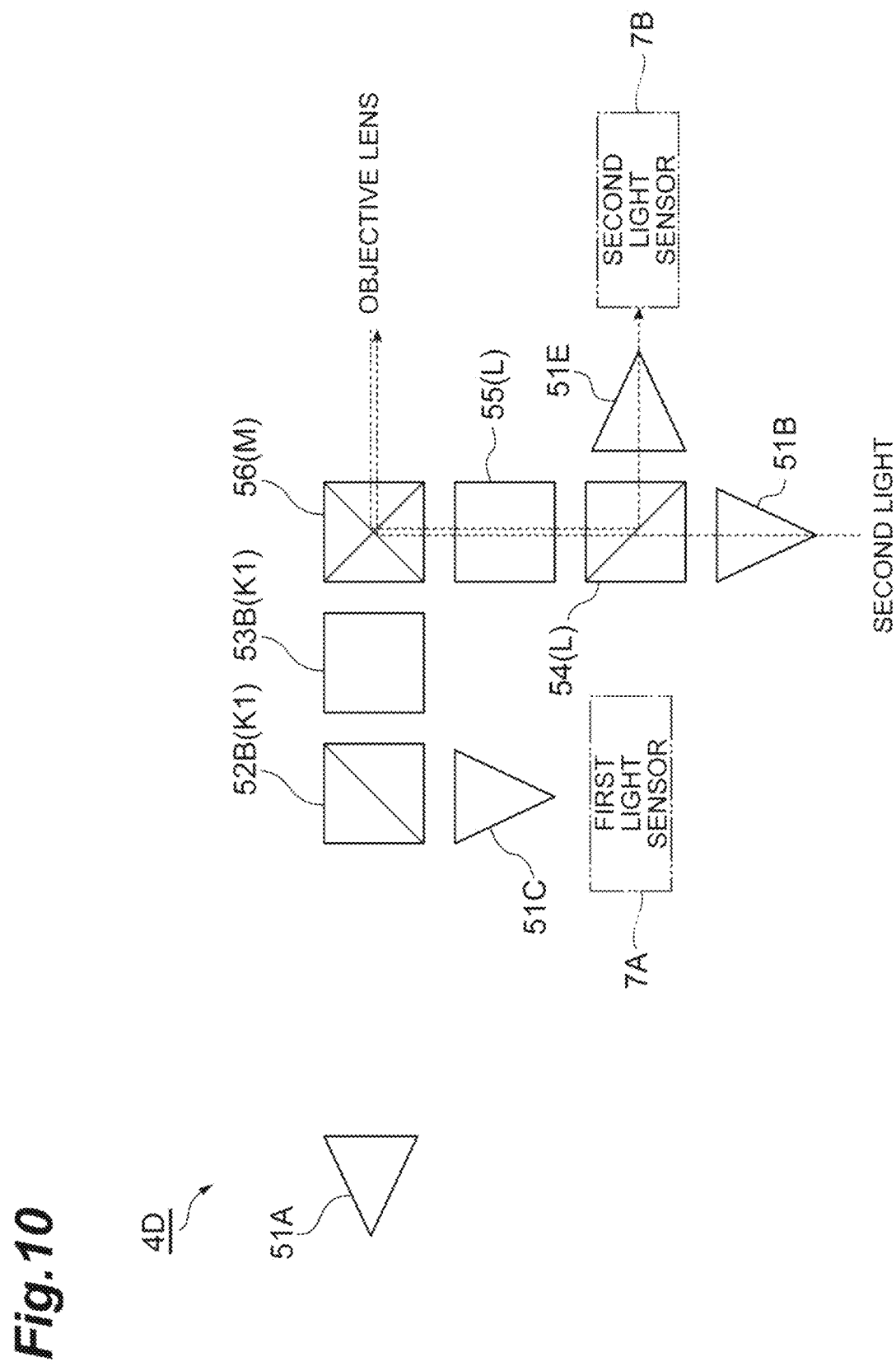
FIG. 10 is a diagram illustrating an optical path of second light in the light guide optical system in the inspection apparatus according to the fourth embodiment.

An inspection apparatus according to a fourth embodiment is a modified example of the third embodiment. As illustrated in FIGS. 9 and 10, the fourth embodiment is different from the third embodiment in that an arrangement of a polarization control element K2 and a collimator 51D for guiding the other polarized component of first light to a light detection unit 7 is omitted in a light guide optical system 4D. Also, the fourth embodiment is different from the third embodiment in that a polarizing beam splitter 52B of the light guide optical system 4D transmits light having a polarized component of 0° in a polarization plane and reflects light having a polarized component of 90° in a polarization plane. The others are similar to those of the third embodiment.

As illustrated in FIG. 9, only a polarized component of 90° reflected by the polarizing beam splitter 52B in first light whose polarization plane is rotated by 90° in total is output to a first light sensor 7A of the light detection unit 7. Also, as illustrated in FIG. 10, second light which reciprocates in a $\lambda$/4 wavelength plate 55 and becomes linearly polarized light whose polarization plane is rotated by 90° is output to a second light sensor 7B of the light detection unit 7.

Also, in such a form, as in the above-described embodiment, while optical elements having wavelength dependency suitable for a first wavelength and a second wavelength are used in the light guide optical system 4D through an optical path switching element M, optical elements for forming an optical path of the first light and optical elements for forming an optical path of the second light can be partially shared. Therefore, it is possible to accurately perform both detection of the presence/absence of abnormality of the measurement target D and acquisition of a pattern while avoiding complication of a configuration. Such a form is useful when an SN ratio of a light source can be sufficiently secured. In such a form, it is possible to reduce the number of optical elements used for the light guide optical system 4D and simplify the configuration.

Fifth Embodiment

Figure 11:
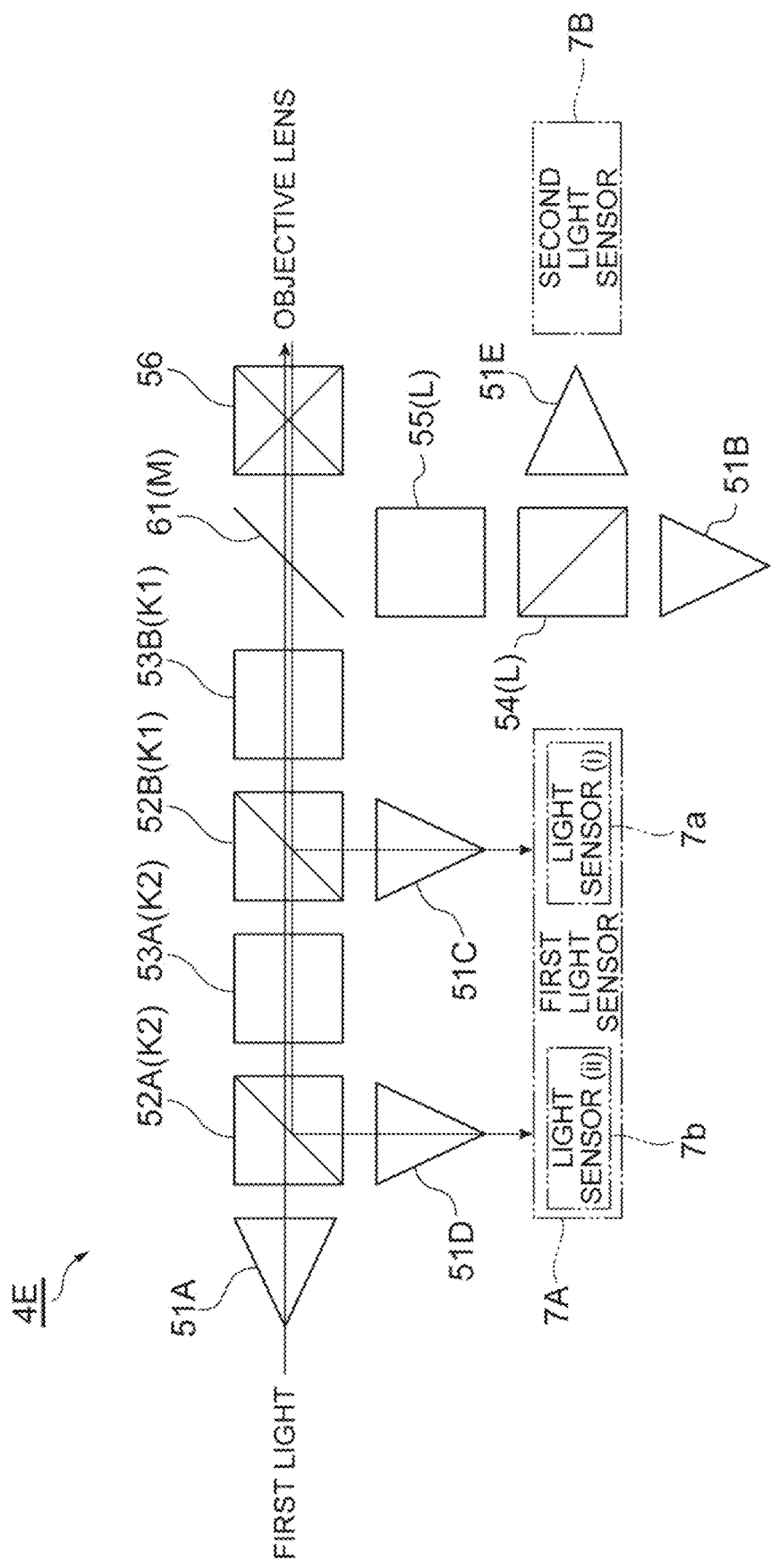
FIG. 11 is a diagram illustrating an optical path of first light in a light guide optical system in an inspection apparatus according to a fifth embodiment.
Figure 12:
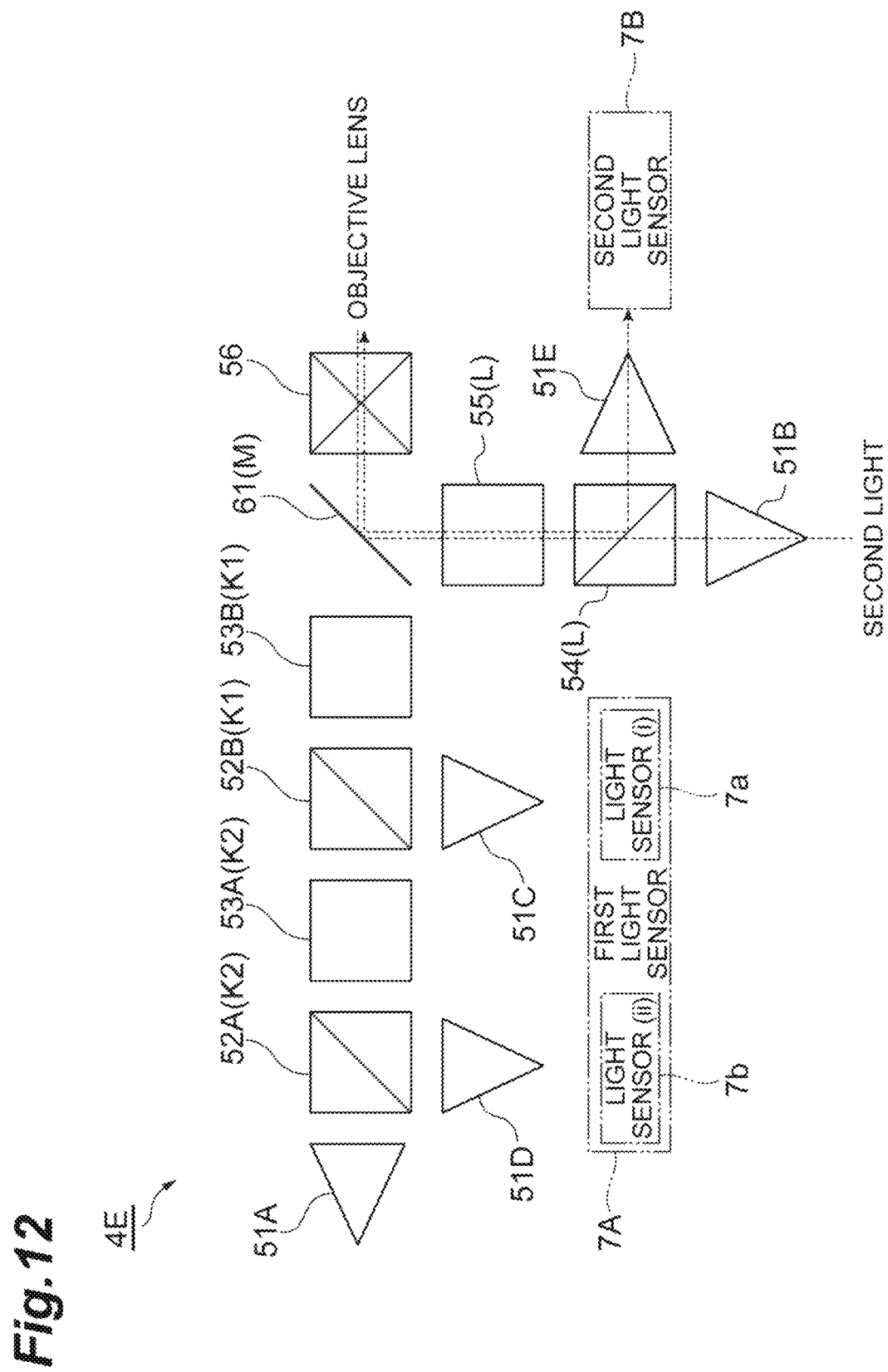
FIG. 12 is a diagram illustrating an optical path of second light in the light guide optical system in the inspection apparatus according to the fifth embodiment.

As illustrated in FIGS. 11 and 12, an inspection apparatus according to a fifth embodiment is different from that according to the above-described embodiment in that an optical path switching element M includes a dichroic mirror 61 in a light guide optical system 4E. The light guide optical system 4E has a configuration similar to that of the light guide optical system 4C in the third embodiment, but is different from the light guide optical system 4C of the third embodiment in that the dichroic mirror 61 is arranged between a Faraday rotator 53B and a galvanomirror 56.

The dichroic mirror 61 transmits first light. An optical path of the first light is substantially the same as that of the third embodiment as illustrated in FIG. 11. Polarized components orthogonal to each other in the first light are output to a light sensor (i) 7a and a light sensor (ii) 7b of a first sensor 7A of a light detection unit 7 by a polarization control element K1 and a polarization control element K2 and subjected to differential detection. Also, the dichroic mirror 61 reflects second light. As illustrated in FIG. 12, an optical path of the second light is substantially the same as that of the third embodiment, except that a polarizing beam splitter 54 and a λ/4 wavelength plate 55 are optically coupled to the dichroic mirror 61. The second light which reciprocates in the λ/4 wavelength plate 55 and becomes linearly polarized light whose polarization plane is rotated by 90° is output to a second light sensor 7B of the light detection unit 7.

Also, in such a form, as in the above-described embodiment, while optical elements having wavelength dependency suitable for a first wavelength and a second wavelength are used in the light guide optical system 4E through the optical path switching element M, optical elements for forming the optical path of the first light and optical elements for forming the optical path of the second light can be partially shared. Therefore, it is possible to accurately perform both detection of the presence/absence of abnormality of the measurement target D and acquisition of a pattern while avoiding complication of a configuration. Also, because the optical path switching element M includes only the dichroic mirror 61 and a physical operation is unnecessary, the optical path switching element M can be simply configured.

In the present embodiment, the dichroic mirror 61 and a galvanomirror 56 among optical elements constituting the light guide optical system 4E can be shared between the optical path of the first light and the optical path of the second light. Also, in the light detection unit 7, differential detection of one polarized component of the first light and the other polarized component of the first light can be performed. Therefore, even when an SN ratio of a light source is relatively low, it is possible to accurately detect the presence/absence of abnormality of the measurement target D. Although an amount of detectable light decreases, a half mirror may be used in place of the dichroic mirror 61 in the present embodiment.

Sixth Embodiment

Figure 13:
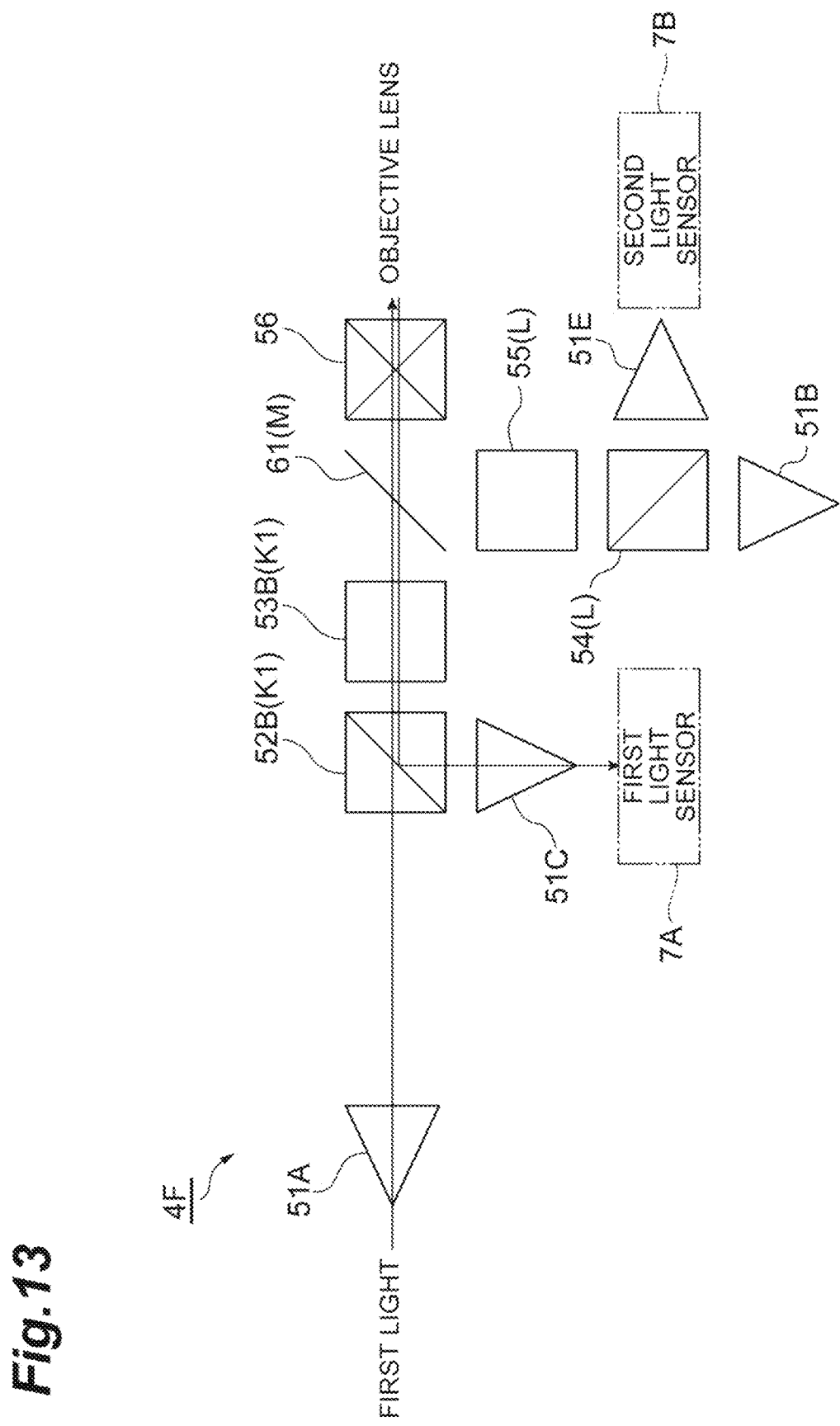
FIG. 13 is a diagram illustrating an optical path of first light in a light guide optical system in an inspection apparatus according to a sixth embodiment.
Figure 14:
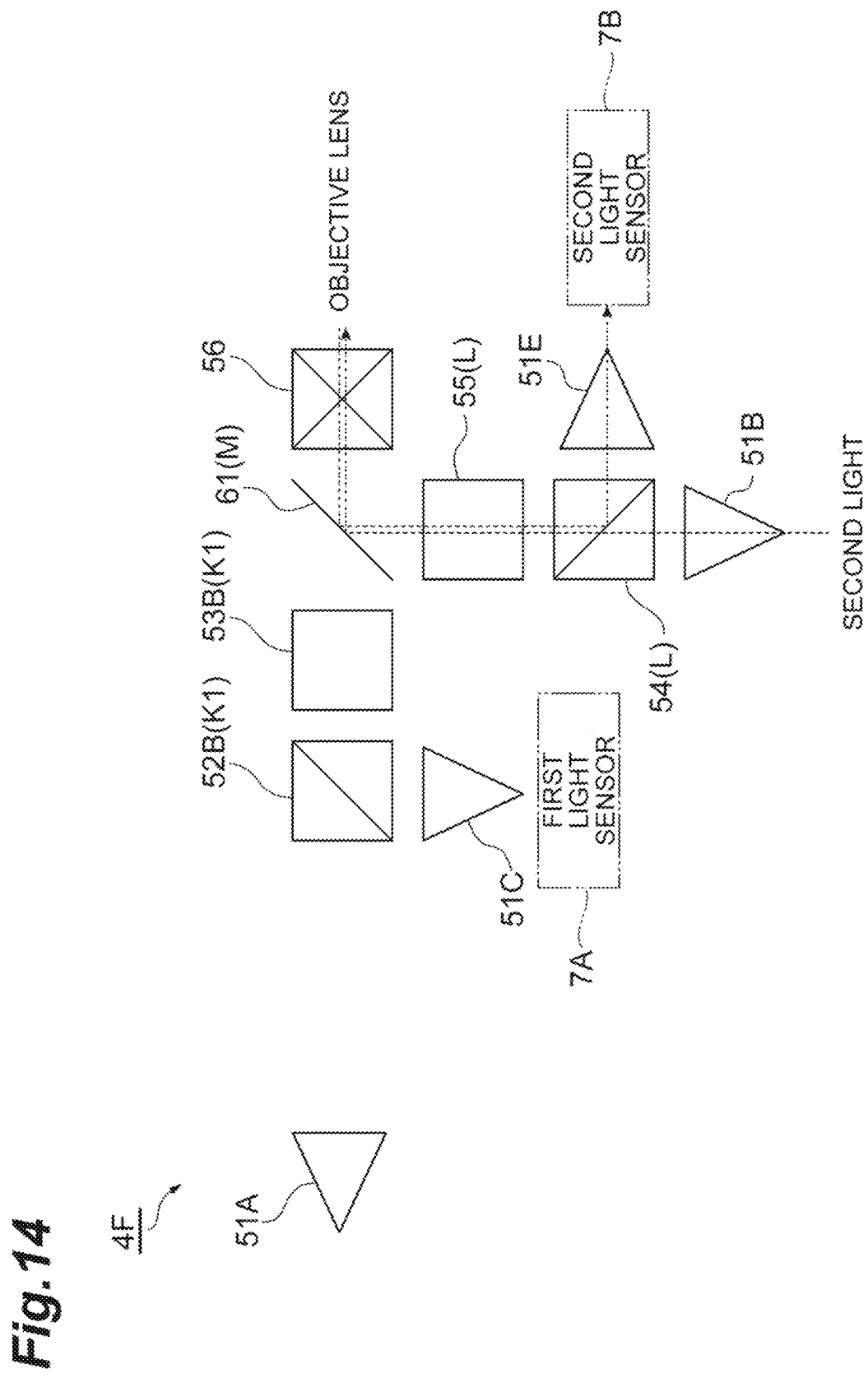
FIG. 14 is a diagram illustrating an optical path of second light in the light guide optical system in the inspection apparatus according to the sixth embodiment.

An inspection apparatus according to a sixth embodiment is a modified example of the fifth embodiment. As illustrated in FIGS. 13 and 14, the sixth embodiment is different from the fifth embodiment in that an arrangement of a polarization control element K2 for guiding the other polarized component of first light to a light detection unit 7 is omitted in a light guide optical system 4F. Also, the sixth embodiment is different from the fifth embodiment in that a polarizing beam splitter 52B of the light guide optical system 4F transmits light having a polarized component of 0° in a polarization plane and reflects light having a polarized component of 90° in a polarization plane. The others are similar to those of the fifth embodiment.

Also, in such a form, as in the above-described embodiment, while optical elements having wavelength dependency suitable for a first wavelength and a second wavelength are used in the light guide optical system 4F through an optical path switching element M, optical elements for forming an optical path of the first light and optical elements for forming an optical path of second light can be partially shared. Therefore, it is possible to accurately perform both detection of the presence/absence of abnormality of a measurement target D and acquisition of a pattern while avoiding complication of a configuration. Such a form is useful when an SN ratio of a light source can be sufficiently secured. In such a form, it is possible to reduce the number of optical elements used for the light guide optical system 4F and simplify a configuration.

Seventh Embodiment

Figure 15:
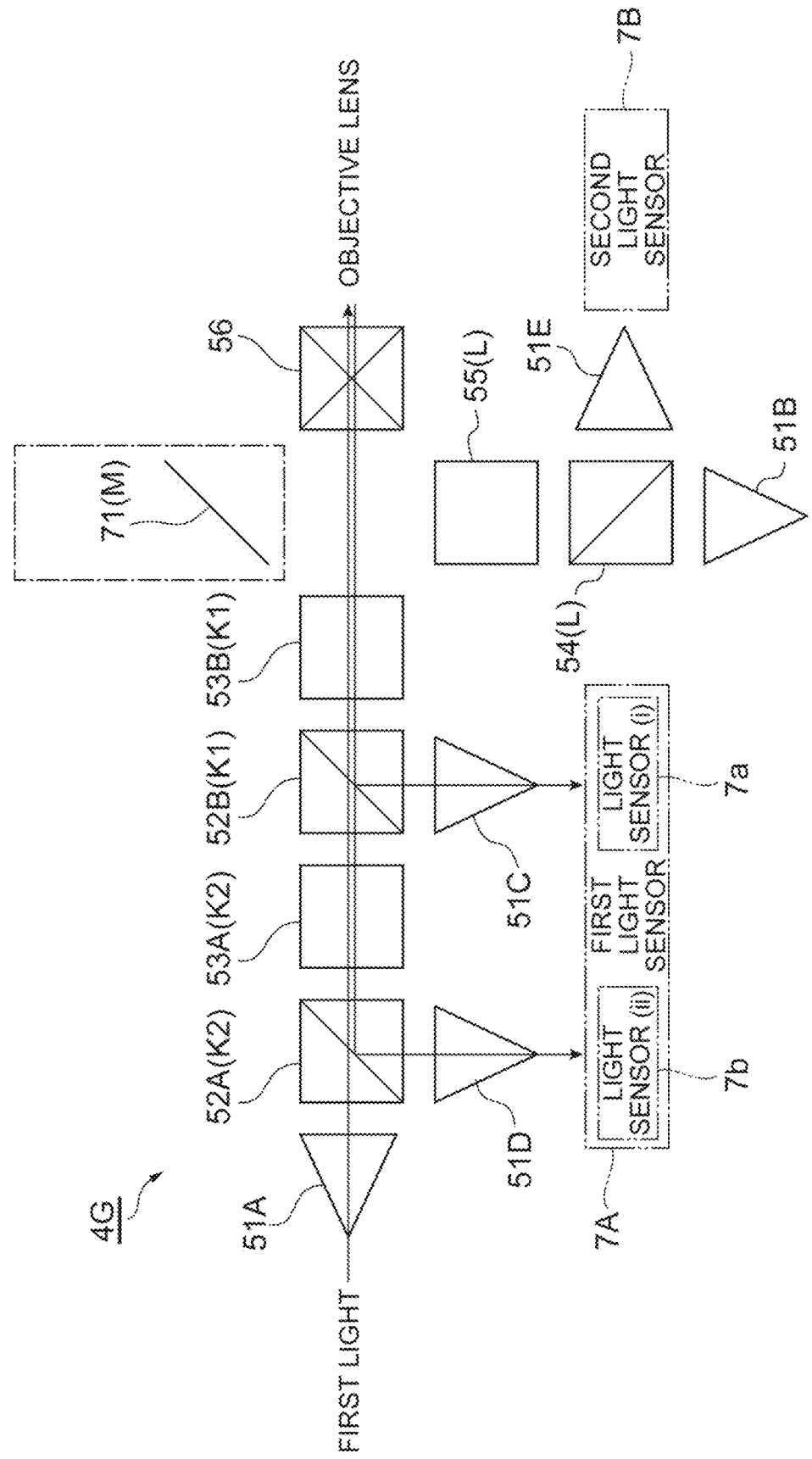
FIG. 15 is a diagram illustrating an optical path of first light in a light guide optical system in an inspection apparatus according to a seventh embodiment.
Figure 16:
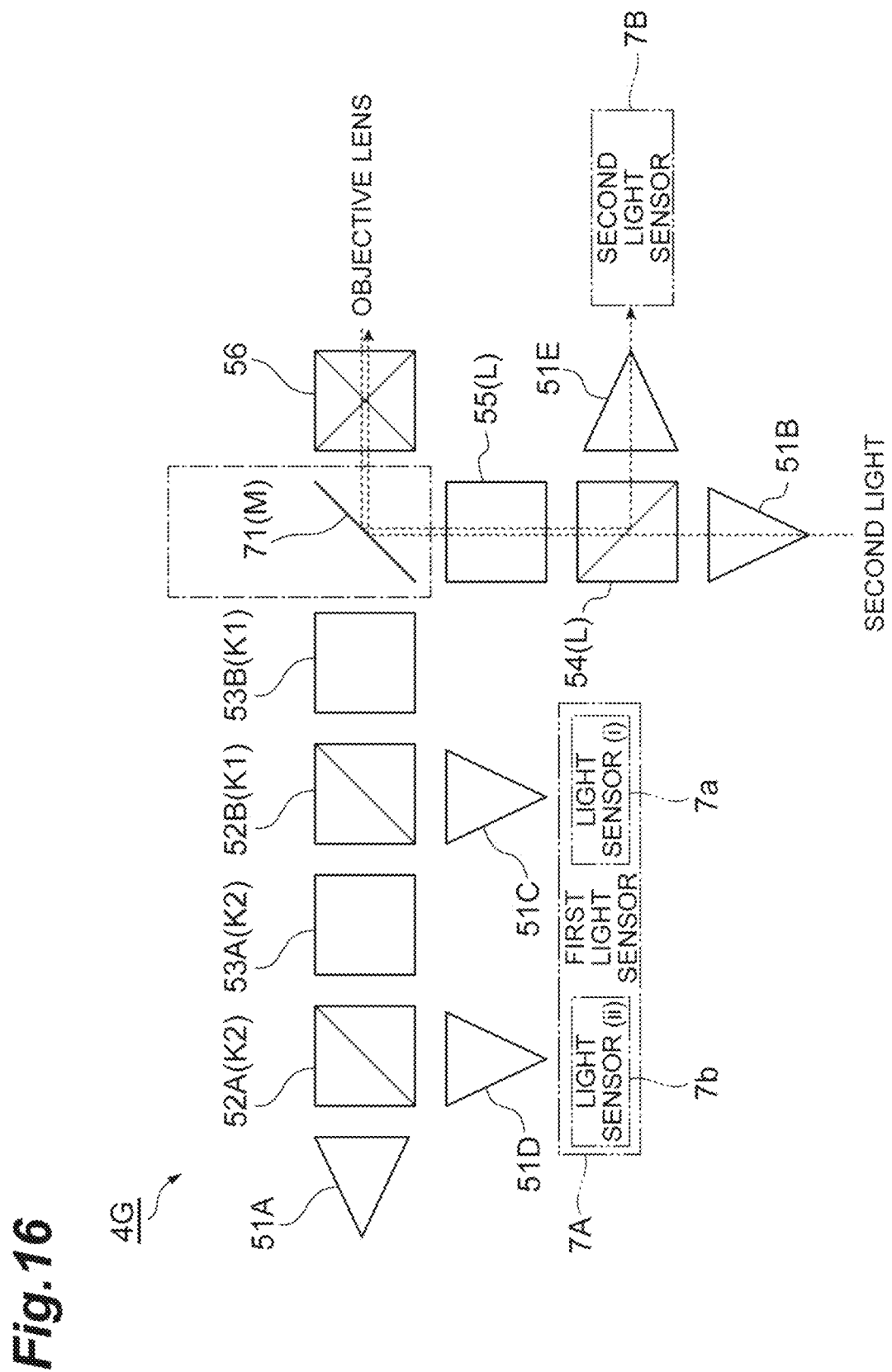
FIG. 16 is a diagram illustrating an optical path of second light in the light guide optical system in the inspection apparatus according to the seventh embodiment.

As illustrated in FIGS. 15 and 16, an inspection apparatus according to a seventh embodiment is different from the above-described embodiment in that an optical path switching element M includes an optical mirror 71 in a light guide optical system 4G. The light guide optical system 4G has a configuration similar to that of the light guide optical system 4E in the fifth embodiment, but is different from the light guide optical system 4E of the fifth embodiment in that the optical mirror 71 is arranged instead of the dichroic mirror 61.

For example, the optical mirror 71 is configured so that switching is performed between advancement and retraction to and from the optical path by a driving means such as a cylinder. If first light is output from a light output unit 3, the optical mirror 71 is retracted from the optical path as illustrated in FIG. 15. The optical path of the first light is substantially the same as that of the fifth embodiment. Polarized components orthogonal to each other in the first light are output to a light sensor (i) 7a and a light sensor (ii) 7b of a first light sensor 7A of a light detection unit 7 by a polarization control element K1 and a polarization control element K2 and subjected to differential detection.

If the second light is output from the light output unit 3, the optical mirror 71 is advanced to the optical path. The optical mirror 71 reflects second light. As illustrated in FIG. 16, an optical path of the second light is substantially the same as that of the fifth embodiment, except that a polarizing beam splitter 54 and a λ/4 wavelength plate 55 are optically coupled to the optical mirror 71. The second light which reciprocates in the λ/4 wavelength plate 55 and becomes linearly polarized light whose polarization plane is rotated by 90° is output to a second light sensor 7B of the light detection unit 7.

Also, in such a form, as in the above-described embodiment, while optical elements having wavelength dependency suitable for a first wavelength and a second wavelength are used in the light guide optical system 4G through an optical path switching element M, optical elements for forming the optical path of the first light and optical elements for forming the optical path of the second light can be partially shared. Therefore, it is possible to accurately perform both detection of the presence/absence of abnormality of a measurement target D and acquisition of a pattern while avoiding complication of a configuration. Also, because the optical path switching element M is configured only for advancement/retraction of the optical mirror 71, the optical path switching element M can be simply configured.

In the present embodiment, the optical mirror 71 and a galvanomirror 56 among optical elements constituting the light guide optical system 4G can be shared between the optical path of the first light and the optical path of the second light. Also, in the light detection unit 7, differential detection of one polarized component of the first light and the other polarized component of the first light can be performed. Therefore, even when an SN ratio of a light source is relatively low, it is possible to accurately detect the presence/absence of abnormality of the measurement target D.

Eighth Embodiment

Figure 17:
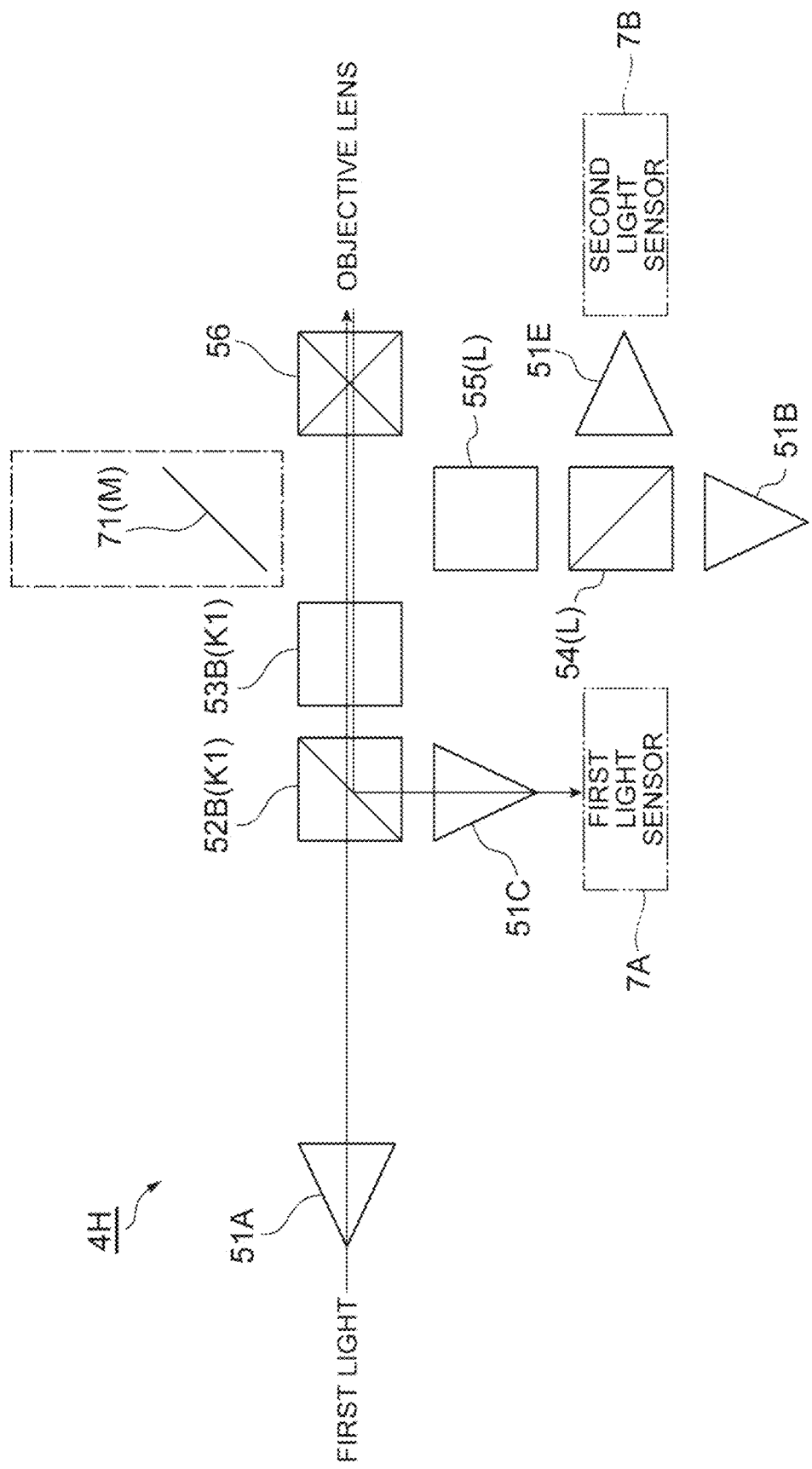
FIG. 17 is a diagram illustrating an optical path of first light in a light guide optical system in an inspection apparatus according to an eighth embodiment.
Figure 18:
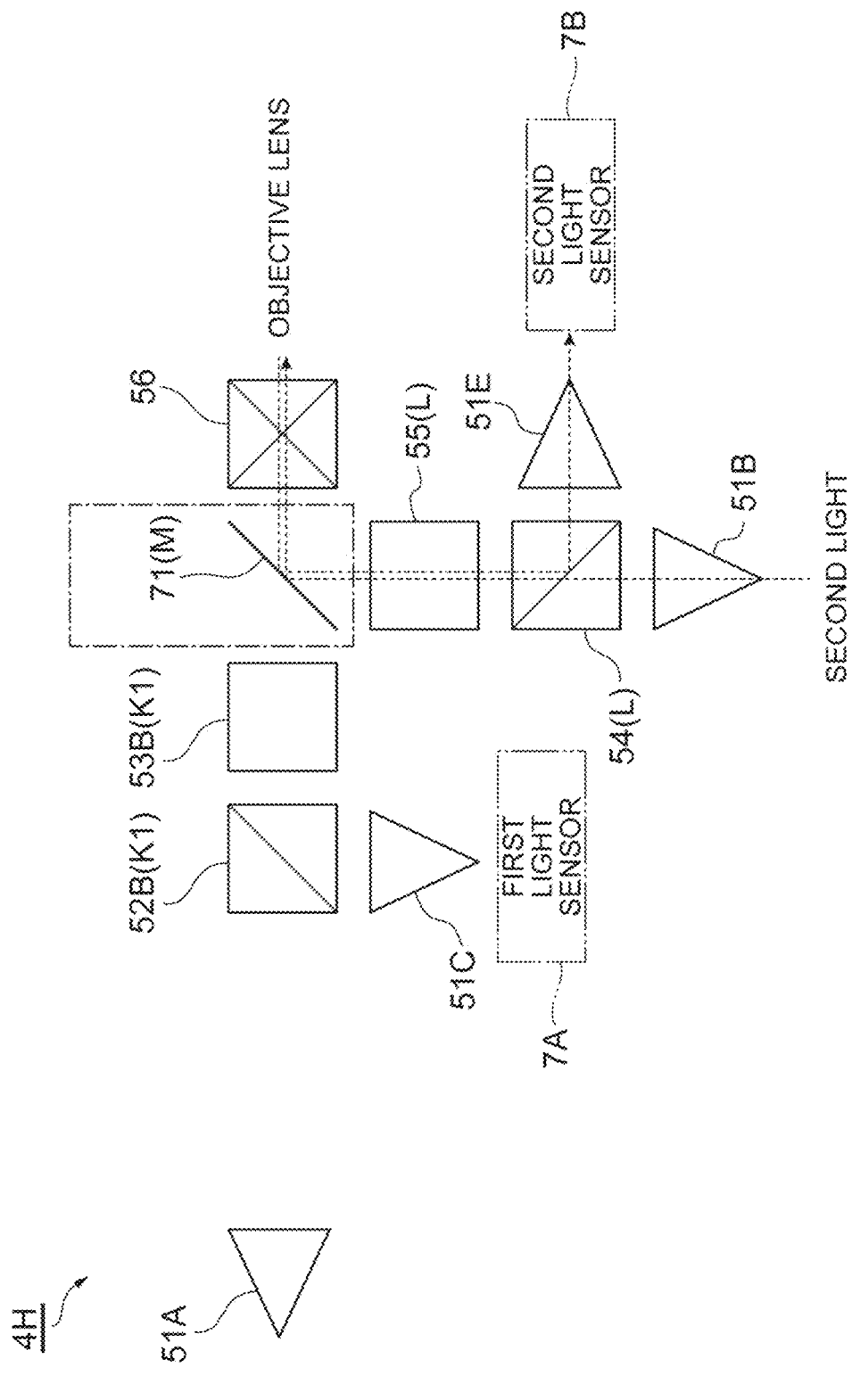
FIG. 18 is a diagram illustrating an optical path of second light in the light guide optical system in the inspection apparatus according to the eighth embodiment.

An inspection apparatus according to an eighth embodiment is a modified example of the seventh embodiment. As illustrated in FIGS. 17 and 18, the eighth embodiment is different from the seventh embodiment in that an arrangement of a polarization control element K2 for guiding the other polarized component of first light to a light detection unit 7 is omitted in a light guide optical system 4H. Also, the eighth embodiment is different from the seventh embodiment in that a polarizing beam splitter 52B of the light guide optical system 4H transmits light having a polarized component of 0° in a polarization plane and reflects light having a polarized component of 90° in a polarization plane. The others are similar to those of the seventh embodiment.

Also, in such a form, as in the above-described embodiment, while optical elements having wavelength dependency suitable for a first wavelength and a second wavelength are used in the light guide optical system 4H through an optical path switching element M, optical elements for forming an optical path of the first light and optical elements for forming an optical path of second light can be partially shared. Therefore, it is possible to accurately perform both detection of the presence/absence of abnormality of a measurement target D and acquisition of a pattern while avoiding complication of a configuration. Such a form is useful when an SN ratio of a light source can be sufficiently secured. In such a form, it is possible to reduce the number of optical elements used for the light guide optical system 4H and simplify a configuration.

Ninth Embodiment

An inspection apparatus according to a ninth embodiment is different from the above-described embodiment in the configuration of a light guide optical system 4I. In the light guide optical system 4I, as in the first embodiment, an optical path switching element M includes a Faraday rotator and a λ/4 wavelength plate. A configuration of the light guide optical system 4I is similar to that of the fifth embodiment, and the Faraday rotator 53B and the λ/4 wavelength plate 55 are arranged in a stage previous to a galvanomirror 56 as the optical path switching element M. One of the Faraday rotator 53B and the λ/4 wavelength plate 55 is advanced to an optical path by a driving means such as a cylinder, and the other is retracted from the optical path.

A dichroic mirror 61 is arranged between a polarizing beam splitter 52B and the optical path switching element M. The Faraday rotator 53B constitutes the optical path switching element M, cooperates with the polarizing beam splitter 52B, and constitutes a polarization control element K1 configured to guide one polarized component of the first light to a light detection unit 7. The λ/4 wavelength plate 55 constitutes the optical path switching element M, cooperates with a polarizing beam splitter 54, and constitutes a polarization control element L configured to guide one polarized component of the second light to the light detection unit 7.

Figure 19:
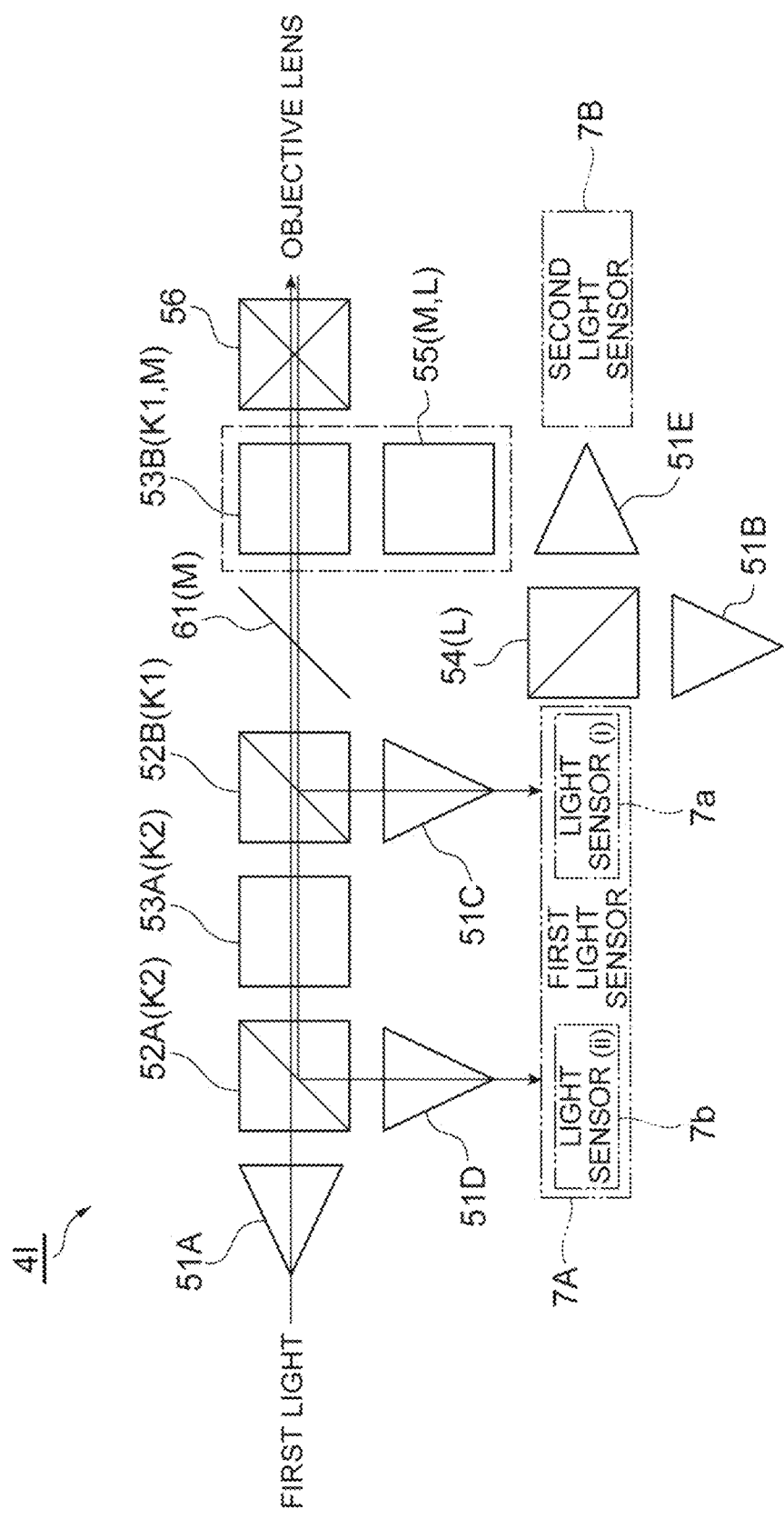
FIG. 19 is a view illustrating an optical path of first light in a light guide optical system in an inspection apparatus according to a ninth embodiment.

If first light is output from a light output unit 3, the Faraday rotator 53B is advanced to an optical path of the light guide optical system 4I in the optical path switching element M as illustrated in FIG. 19. The dichroic mirror 61 transmits the first light. An optical path of the first light is substantially the same as that of the fifth embodiment, except that a positional relationship between the dichroic mirror 61 and the Faraday rotator 53B is reversed. Polarized components orthogonal to each other in the first light are output to a light sensor (i) 7a and a light sensor (ii) 7b of a first light sensor 7A of the light detection unit 7 by the polarization control element K1 and a polarization control element K2 and subjected to differential detection.

Figure 20:
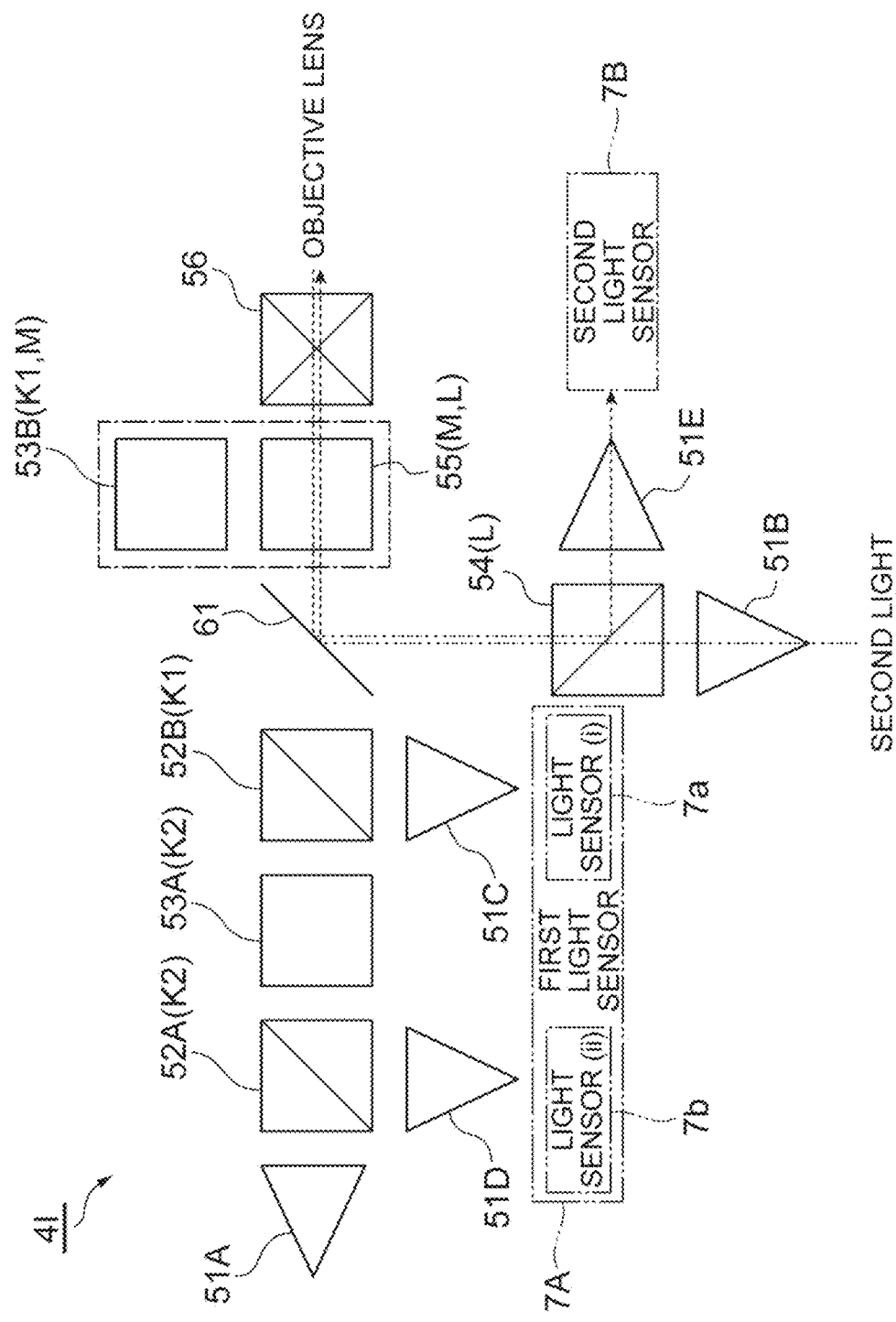
FIG. 20 is a diagram illustrating an optical path of second light in the light guide optical system in the inspection apparatus according to the ninth embodiment.

If second light is output from the light output unit 3, the λ/4 wavelength plate 55 is advanced to the optical path of the light guide optical system 4I in the optical path switching element M as illustrated in FIG. 20. An optical path of the second light is substantially the same as that of the fifth embodiment, except that a positional relationship between the dichroic mirror 61 and the λ/4 wavelength plate 55 is reversed with respect thereto. The second light which reciprocates in the λ/4 wavelength plate 55 and becomes light linearly polarized by 90° is output to a second light sensor 7B of the light detection unit 7.

Also, in such a form, as in the above-described embodiment, while optical elements having wavelength dependency suitable for a first wavelength and a second wavelength are used in the light guide optical system 4I through the optical path switching element M, optical elements for forming the optical path of the first light and optical elements for forming the optical path of the second light can be partially shared. Therefore, it is possible to accurately perform both detection of the presence/absence of abnormality of a measurement target D and acquisition of a pattern while avoiding complication of a configuration.

In the present embodiment, the dichroic mirror 61 and a galvanomirror 56 among optical elements constituting the light guide optical system 4I can be shared between the optical path of the first light and the optical path of the second light. Also, in the light detection unit 7, differential detection of one polarized component of the first light and the other polarized component of the first light can be performed. Therefore, even when an SN ratio of a light source is relatively low, it is possible to accurately detect the presence/absence of abnormality of the measurement target D.

Tenth Embodiment

Figure 21:
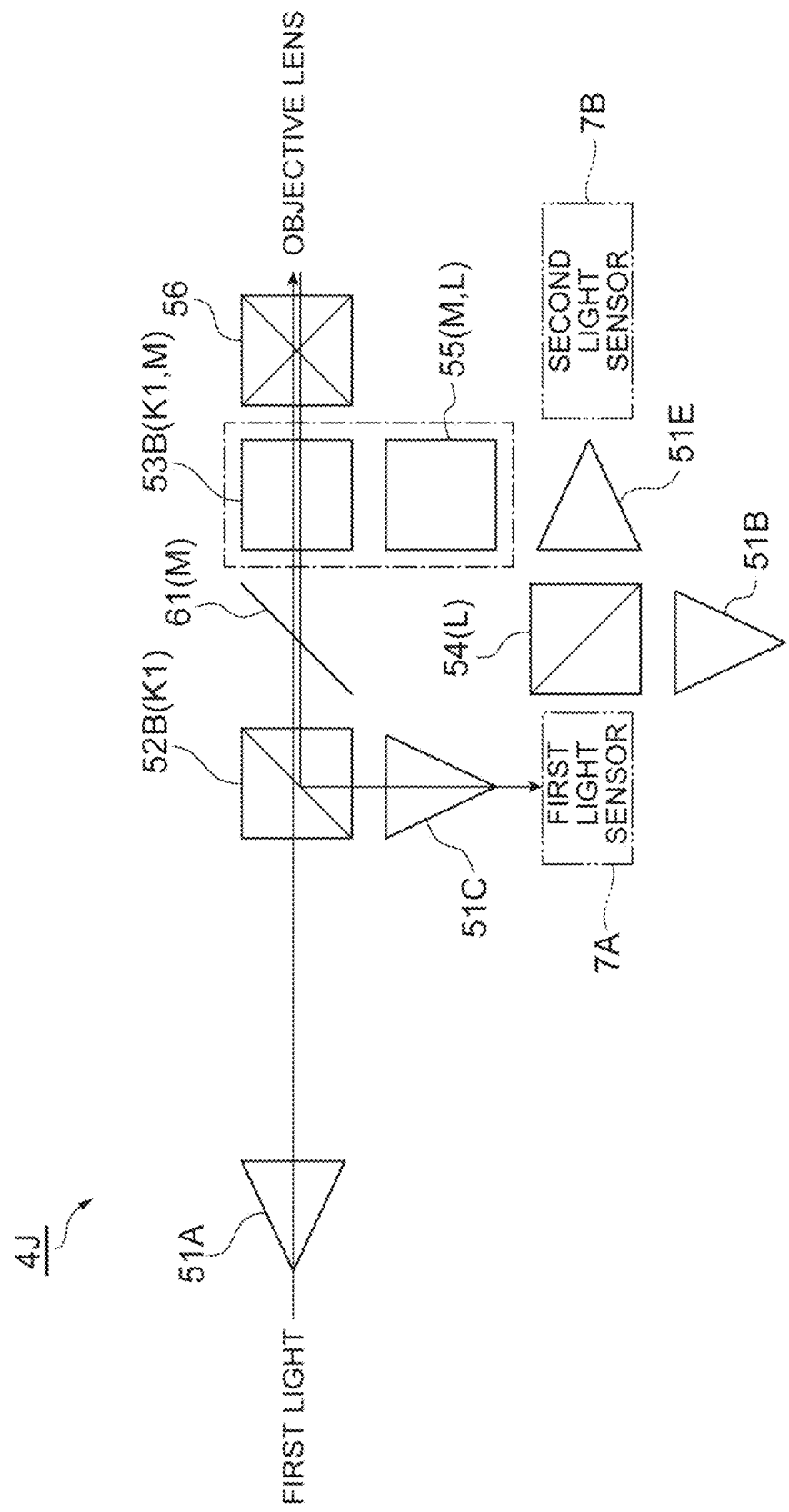
FIG. 21 is a diagram illustrating an optical path of first light in a light guide optical system in an inspection apparatus according to a tenth embodiment.
Figure 22:
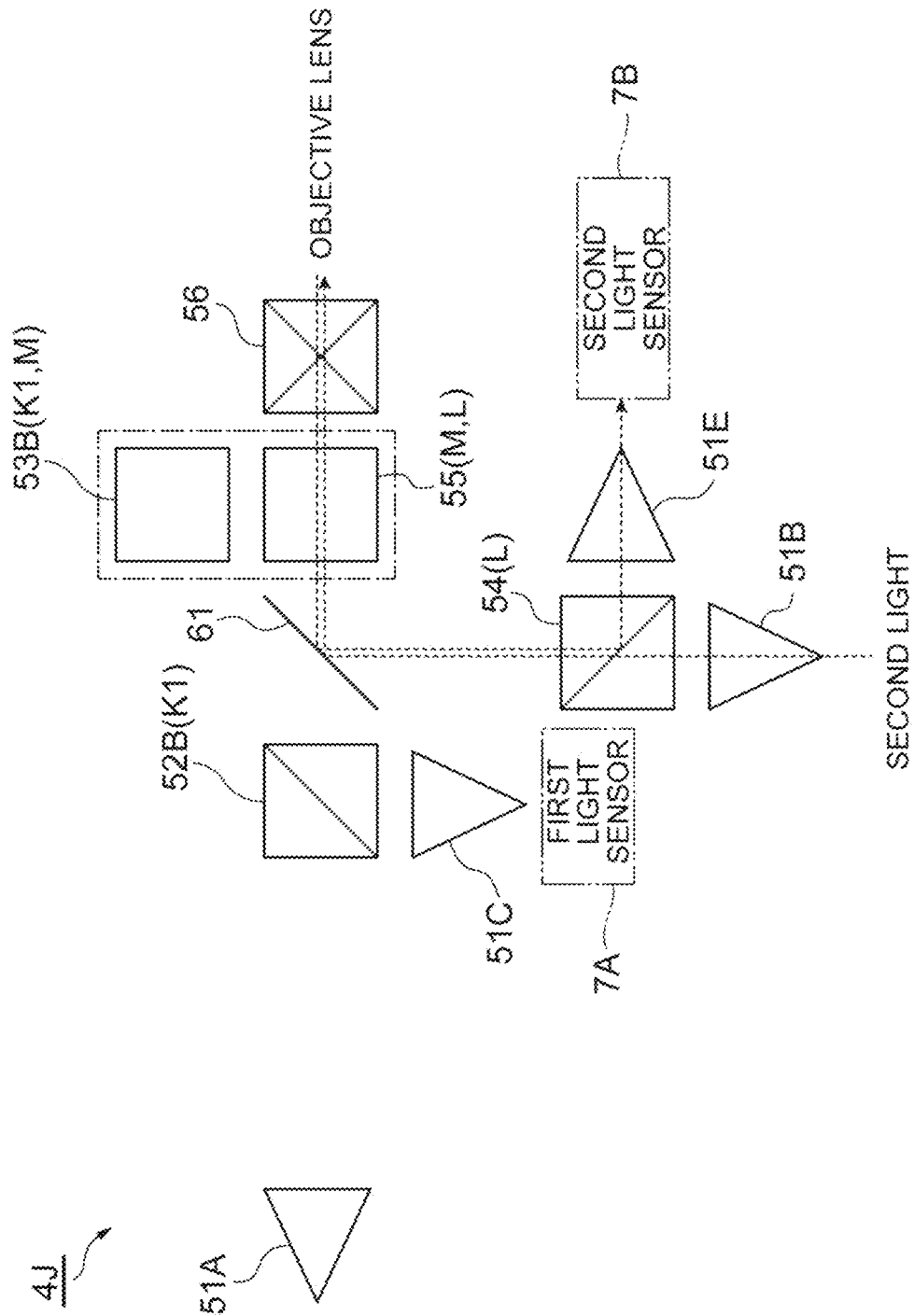
FIG. 22 is a view illustrating an optical path of second light in the light guide optical system in the inspection apparatus according to the tenth embodiment.

An inspection apparatus according to a tenth embodiment is a modified example of the ninth embodiment. As illustrated in FIGS. 21 and 22, the tenth embodiment is different from the ninth embodiment in that an arrangement of a polarization control element K2 for guiding the other polarized component of first light to a light detection unit 7 is omitted in a light guide optical system 4J. Also, the tenth embodiment is different from the ninth embodiment in that a polarizing beam splitter 52B of the light guide optical system 4J transmits light having a polarized component of 0° in a polarization plane and reflects light having a polarized component of 90° in a polarization plane. The others are similar to those of the ninth embodiment.

Also, in such a form, as in the above-described embodiment, while optical elements having wavelength dependency suitable for a first wavelength and a second wavelength are used in the light guide optical system 4J through an optical path switching element M, optical elements for forming an optical path of first light and optical elements for forming an optical path of second light can be partially shared. Therefore, it is possible to accurately perform both detection of the presence/absence of abnormality of a measurement target D and acquisition of a pattern while avoiding complication of a configuration. Such a form is useful when an SN ratio of a light source can be sufficiently secured. In such a form, it is possible to reduce the number of optical elements used for the light guide optical system 4J and simplify a configuration.

Eleventh Embodiment

Figure 23:
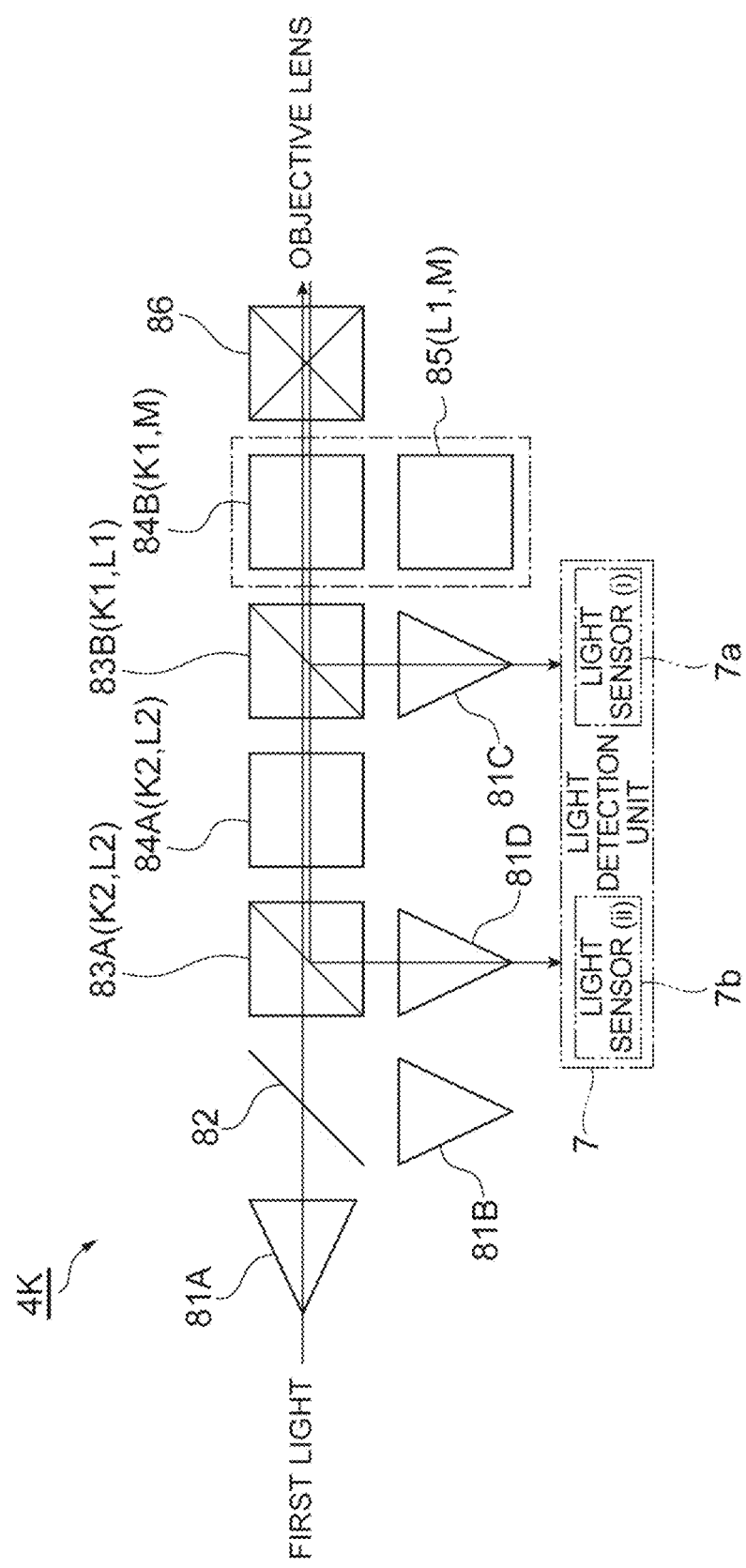
FIG. 23 is a diagram illustrating an optical path of first light in a light guide optical system in an inspection apparatus according to an eleventh embodiment.
Figure 24:
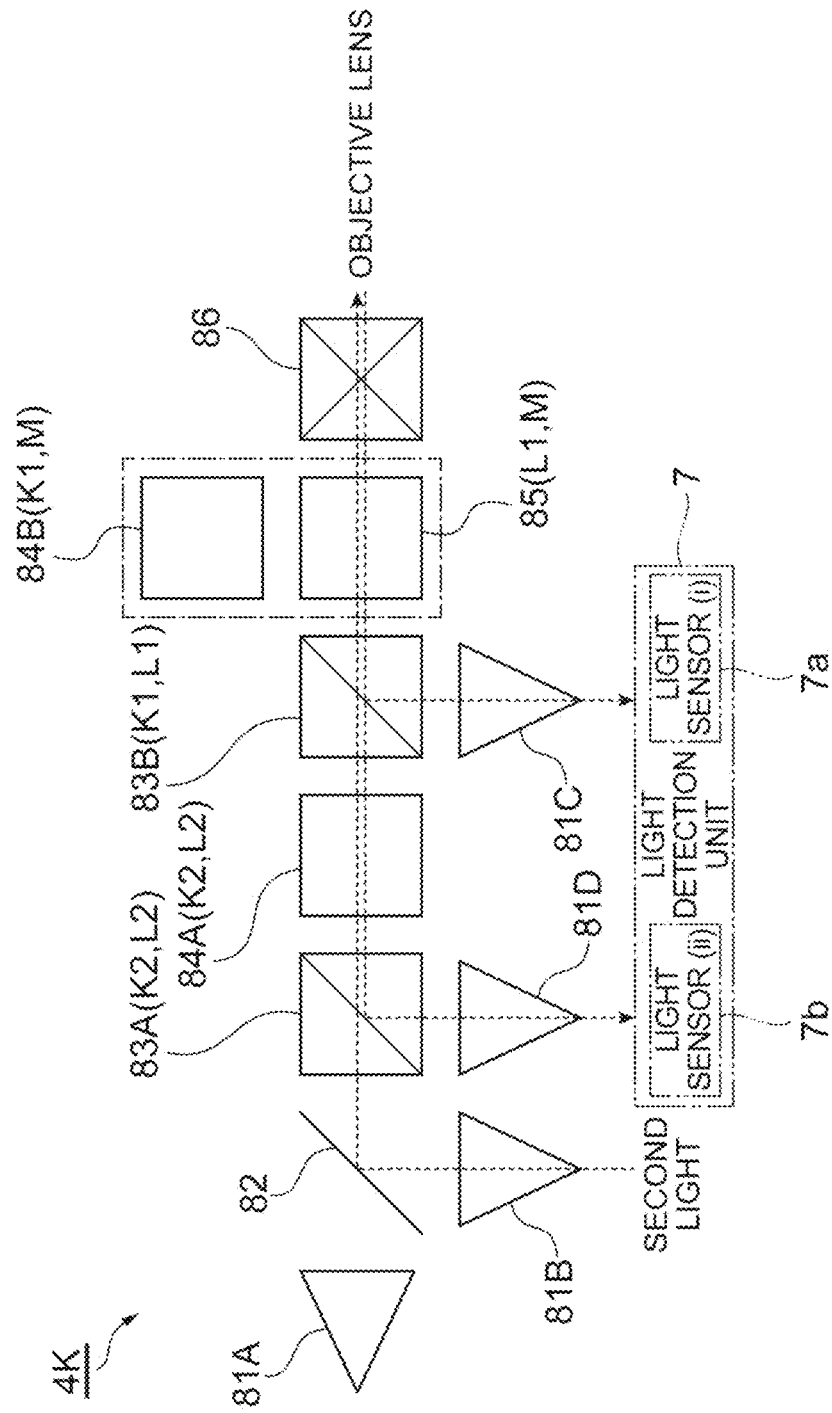
FIG. 24 is a diagram illustrating an optical path of second light in the light guide optical system in the inspection apparatus according to the eleventh embodiment.

An inspection apparatus according to an eleventh embodiment is a modified example of the first embodiment and is different from that according to the first embodiment in that a polarization control element K1 configured to guide one polarized component of first light to a light detection unit 7, and a polarization control element K2 configured to guide the other polarized light component of the first light to the light detection unit 7 are arranged in a light guide optical system 4K as illustrated in FIGS. 23 and 24. Also, the eleventh embodiment is different from the first embodiment in that a polarization control element L1 configured to guide one polarized component of second light to the light detection unit 7, and a polarization control element L2 configured to guide the other polarized light component of the second light to the light detection unit 7 are arranged.

More specifically, the light guide optical system 4K includes collimators 81A to 81D, a dichroic mirror 82, polarizing beam splitters 83A and 83B, Faraday rotators 84A and 84B, a λ/4 wavelength plate 85, and a galvanomirror 86 as a plurality of optical elements. Also, the light detection unit 7 has a light sensor (i) 7a and a light sensor (ii) 7b.

The Faraday rotator 84B and the λ/4 wavelength plate 85 are arranged in a stage previous to the galvanomirror 86 as the optical path switching element M. As in the first embodiment, one of the Faraday rotator 84B and the λ/4 wavelength plate 85 is advanced to an optical path by a driving means such as a cylinder and the other is retracted from the optical path.

The polarizing beam splitter 83B and the Faraday rotator 84B constitute the polarization control element K1 configured to guide the one polarized component of the first light to the light sensor (i) 7a of the light detection unit 7. The polarizing beam splitter 83A and the Faraday rotator 84A are arranged in a stage previous to the polarization control element K1 and constitute the polarization control element K2 configured to guide the other polarized component of the first light to the light sensor (ii) 7b of the light detection unit 7.

The polarizing beam splitter 83B and the λ/4 wavelength plate 85 constitute a polarization control element L1 configured to guide the one polarized component of the second light to the light sensor (i) 7a of the light detection unit 7. The polarizing beam splitter 83A and the Faraday rotator 84A constitute a polarization control element L2 configured to guide the other polarized component of the second light to the light sensor (ii) 7b of the light detection unit 7. The dichroic mirror 82 is arranged in a stage previous to the polarization control elements K2 and L2.

If the first light is output from a light output unit 3, the Faraday rotator 84B is advanced to the optical path of the light guide optical system 4K in the optical path switching element M as illustrated in FIG. 23. The first light is light linearly polarized by 0° in an initial state. The first light is collimated by the collimator 81A and is transmitted through the dichroic mirror 82 and the polarizing beam splitter 83A, and a polarization plane of the first light is rotated by 45° by the Faraday rotator 84A. Also, the first light is transmitted through the polarizing beam splitter 83B and guided to the objective lens 5 after the polarization plane of the first light is rotated by 22.5° by the Faraday rotator 84B. A position at which the first light is incident on the objective lens 5, i.e., a position at which the first light is incident on a magneto-optical crystal 6, is scanned by the galvanomirror 86.

The polarization plane of the first light reflected by a reflection film 13 of the magneto-optical crystal 6 is rotated by α° in accordance with the magneto-optical effect (a Kerr effect, a Faraday effect, and the like) according to a magnetic field (a magnetic field intensity) generated in the measurement target D and incident on the light guide optical system 4K through the objective lens 5 again. The polarization plane of the first light is further rotated by 22.5° by the Faraday rotator 84B. Only a polarized component of 135° in the first light whose polarization plane is rotated by 90+α° by reciprocating in the Faraday rotator 84B is reflected by the polarizing beam splitter 83B and output to the light sensor (i) 7a of the light detection unit 7 in a state in which the first light is focused by the collimator 81C.

Also, a polarization plane of the polarized component transmitted through the polarizing beam splitter 83B in the first light is further rotated by 45° by the Faraday rotator 84A and the polarized component is reflected by the polarizing beam splitter 83A and then output to the light sensor (ii) 7b of the light detection unit 7 in a state in which the first light is focused by the collimator 81D. In the light detection unit 7, differential detection of the input light is performed. The light detection unit 7 detects intensity modulation caused by the rotation of the polarization plane by α° in accordance with the magneto-optical effect.

When the second light is output from the light output unit 3, the λ/4 wavelength plate 85 is advanced to the optical path of the light guide optical system 4K in the optical path switching element M as illustrated in FIG. 24. The second light is light linearly polarized by 0° in an initial state. The second light is collimated by the collimator 81B and reflected by the dichroic mirror 82. The second light reflected by the dichroic mirror 82 is transmitted through the polarizing beam splitter 83A and the polarization plane of the second light is rotated by the Faraday rotator 84A. Also, the second light is transmitted through the polarizing beam splitter 83B and guided to the objective lens 5 in a state in which light is circularly polarized by the λ/4 wavelength plate 85. A position at which the second light is incident on the objective lens 5, i.e., a position at which the second light is incident on the measurement target D, is scanned by the galvanomirror 86.

The second light reflected through the inside of the measurement target D is incident on the light guide optical system 4K through the objective lens 5 again. The second light reciprocates in the λ/4 wavelength plate 85 and becomes linearly polarized light whose polarization plane is rotated by 90°. Only the polarized light component of 135° in the second light is reflected by the polarizing beam splitter 83B and is output to the light sensor (i) 7a of the light detection unit 7 in a state in which the second light is focused by the collimator 31C.

Also, a polarization plane of the polarized light component transmitted through the polarizing beam splitter 83B in the second light is further rotated by the Faraday rotator 84A. Only the polarized light component of 90° in the second light is reflected by the polarizing beam splitter 83A and then output to the light sensor (ii) 7b of the light detection unit 7 in a state in which the second light is focused by the collimator 81D.

Also, in such a form, as in the above-described embodiment, while optical elements having wavelength dependency suitable for a first wavelength and a second wavelength are used in the light guide optical system 4K through the optical path switching element M, optical elements for forming the optical path of the first light and optical elements for forming the optical path of the second light can be partially shared. Therefore, it is possible to accurately perform both detection of the presence/absence of abnormality of the measurement target D and acquisition of a pattern while avoiding complication of a configuration.

In the present embodiment, the dichroic mirror 82, the polarizing beam splitters 83A and 83B, the Faraday rotator 84A, and the galvanomirror 86 among the optical elements constituting the light guide optical system 4K are shared between the optical path of the first light and the optical path of the second light. Such a form is useful when the wavelength characteristics of these optical elements and the detection sensitivity of the light detection unit are applicable to both the first light wavelength and the second light wavelength. Also, in the present embodiment, in the light detection unit 7, differential detection of one polarized component of the first light and the other polarized component of the first light can be performed. Therefore, even when an SN ratio of a light source is relatively low, it is possible to accurately detect the presence/absence of abnormality of the measurement target D.

Also, in the present embodiment, in the optical path switching element M, both the light sensor (i) 7a and the light sensor (ii) 7b may simultaneously detect the second light in a state in which the Faraday rotator 84B is advanced to the optical path of the light guide optical system 4K. In this case, the light detection unit 7 can detect an amount of light equivalent to that when the λ/4 wavelength plate 85 is advanced to the optical path of the light guide optical system 4K and only the light sensor (i) 7a detects the second light in the optical path switching element M.

Twelfth Embodiment

Figure 25:
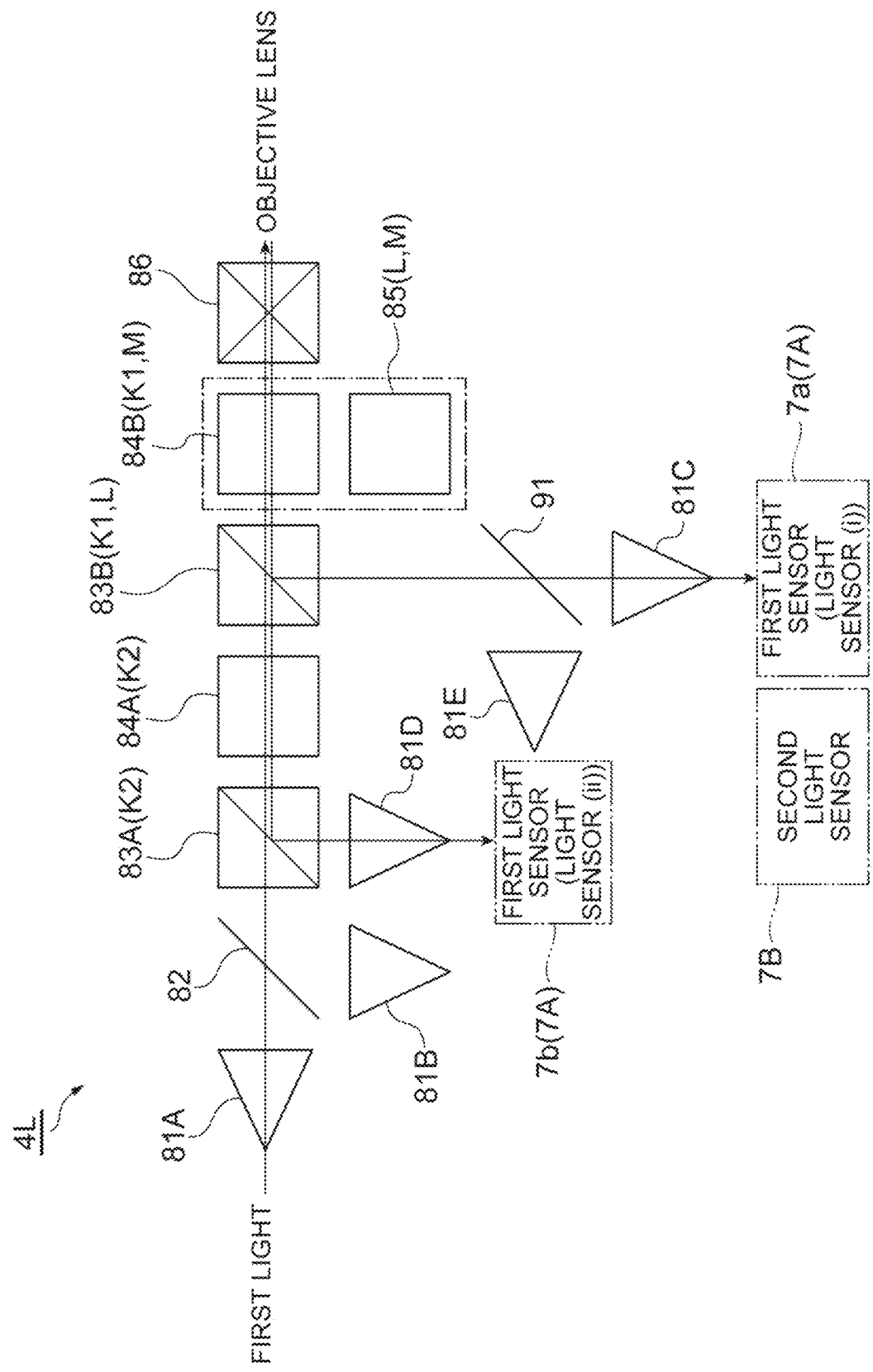
FIG. 25 is a diagram illustrating an optical path of first light in a light guide optical system in an inspection apparatus according to a twelfth embodiment.
Figure 26:
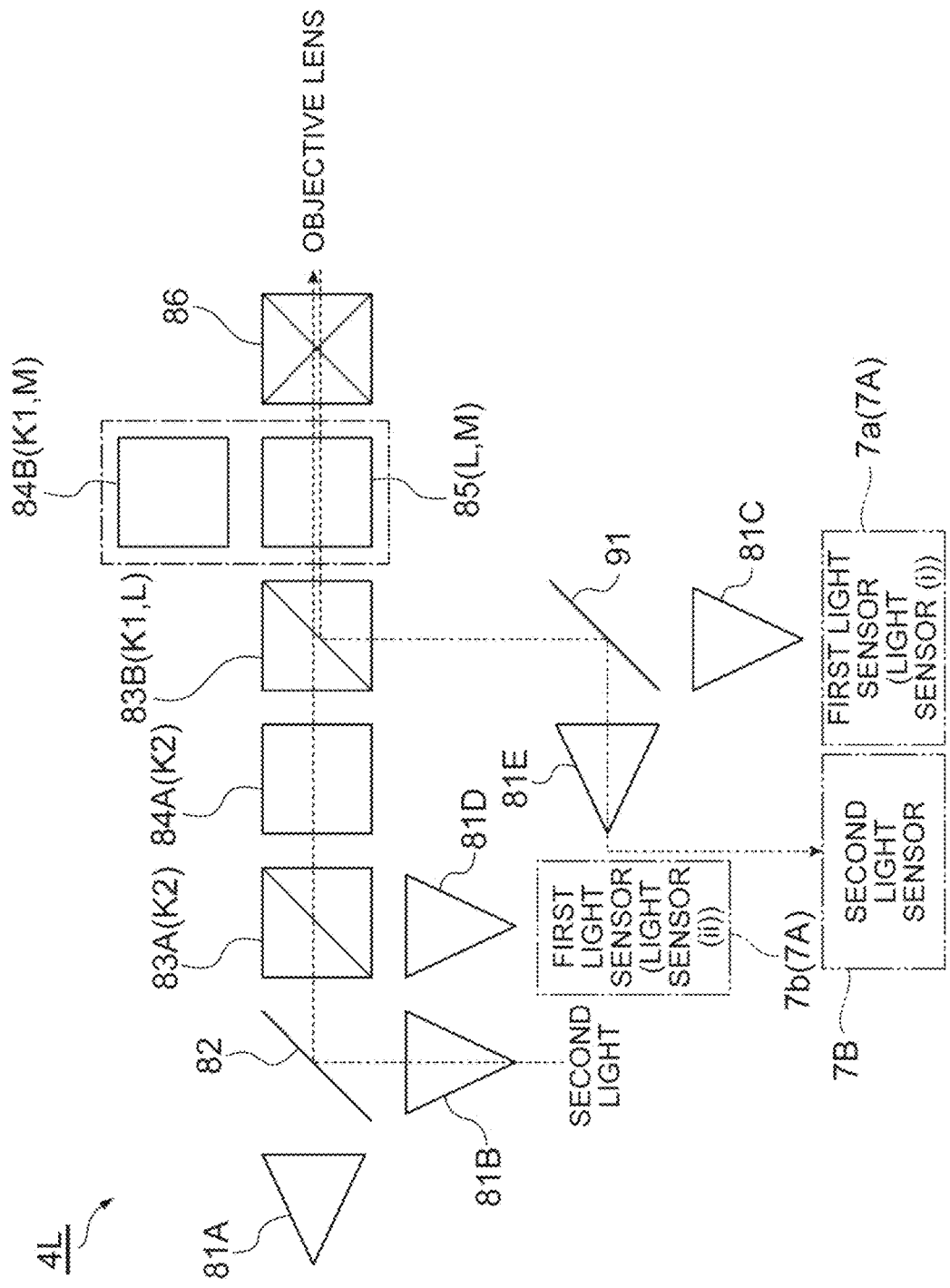
FIG. 26 is a diagram illustrating an optical path of second light in the light guide optical system in the inspection apparatus according to the twelfth embodiment.

An inspection apparatus according to a twelfth embodiment is a modified example of the eleventh embodiment, and is different from that according to the eleventh embodiment in that second light is output to a light detection unit 7 in a light guide optical system 4L as illustrated in FIGS. 25 and 26. More specifically, in the light guide optical system 4L, a dichroic mirror 91 and a collimator 81E are further arranged at an output side of a polarizing beam splitter 83B. Also, in the light guide optical system 4L, the polarizing beam splitter 83B and a λ/4 wavelength plate 85 constitute a polarization control element L configured to guide one polarized component of the second light to the light detection unit 7.

As illustrated in FIG. 25, an optical path of first light is the same as that of the eleventh embodiment, except that a polarized component reflected by the polarizing beam splitter 83B is transmitted through a dichroic mirror 91 and output to a first light sensor 7A of the light detection unit 7. As illustrated in FIG. 26, in an optical path of second light, the polarized component reflected by the polarizing beam splitter 83B is further reflected by the dichroic mirror 91 and output to a second light sensor 7B of the light detection unit 7. The second light which reciprocates in the λ/4 wavelength plate 85 and becomes linearly polarized light whose polarization plane is rotated by 90° is output to the second light sensor 7B of the light detection unit 7 via the collimator 81E.

Also, in such a form, as in the above-described embodiment, an optical element for forming the optical path of the first light and an optical element for forming the optical path of the second light can be partially shared through the optical path switching element M. Therefore, it is possible to accurately perform detection of the presence/absence of abnormality of the measurement target D and acquisition of a pattern while avoiding complication of a configuration.

In the present embodiment, a dichroic mirror 82, polarizing beam splitters 83A and 83B, a Faraday rotator 84A, and a galvanomirror 86 among optical elements constituting the light guide optical system 4L can be shared in the optical paths of the first light and the second light. Such a form is useful when wavelength characteristics of these optical elements can be applied to both the first light wavelength and the second light wavelength. Also, in the present embodiment, in the light detection unit 7 having a light sensor (i) 7a and a light sensor (ii) 7b, it is possible to perform differential detection between one polarized component of the first light and the other polarized component of the first light. Therefore, even when an SN ratio of a light source is relatively low, it is possible to accurately detect the presence/absence of abnormality of the measurement target D.

Furthermore, in the present embodiment, the dichroic mirror 91 is arranged in a stage previous to polarization control elements K1, K2, and L. Thereby, polarization directions of light can be aligned by the polarization control elements K1, K2, and L in a stage subsequent to the dichroic mirror 91. Therefore, the optical path of the first light and the optical path of the second light may be formed at either a reflection side or a transmission side of the dichroic mirror 91, so that a degree of freedom in design of the light guide optical system 4L can be secured.

Thirteenth Embodiment

Figure 27:
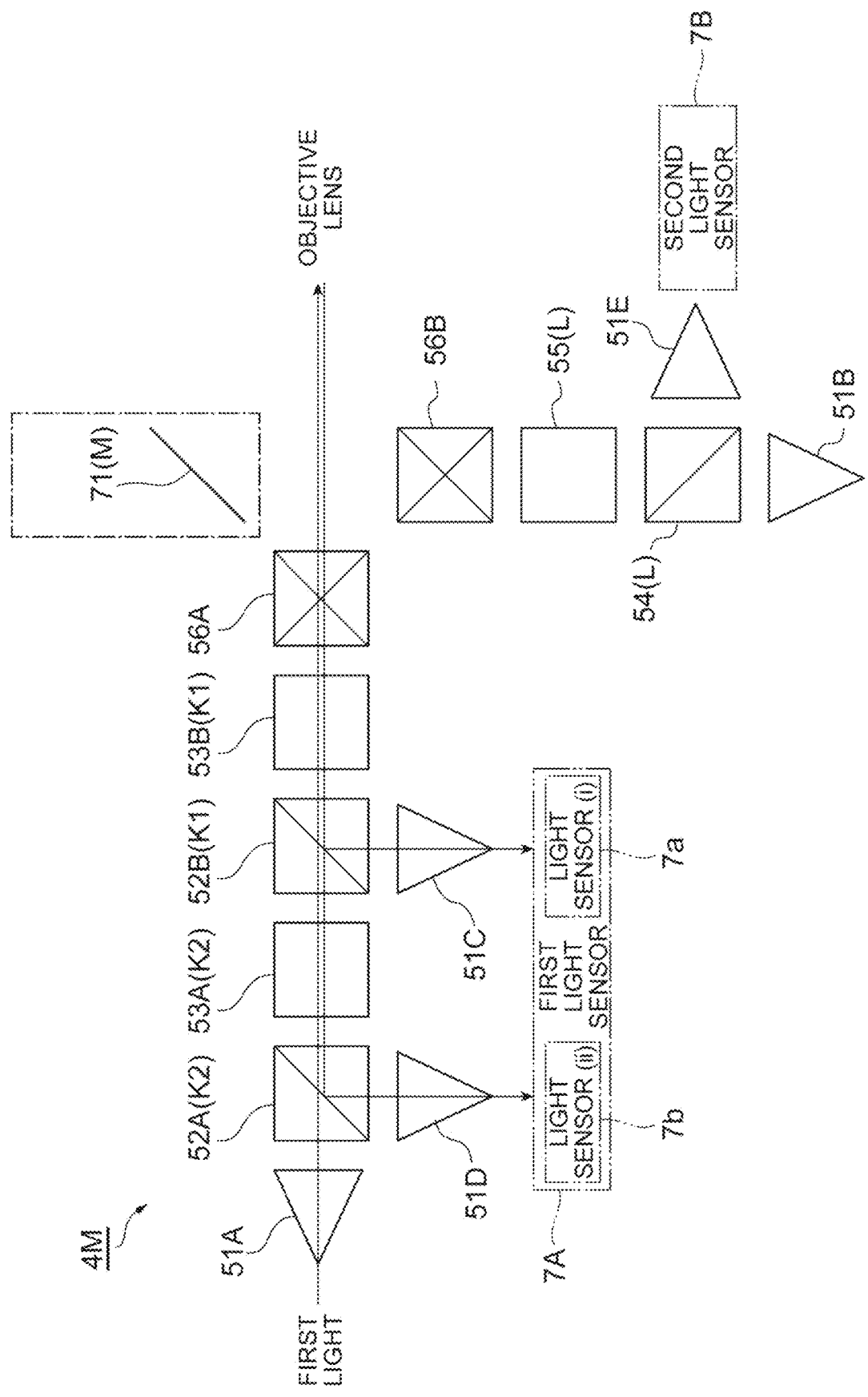
FIG. 27 is a diagram illustrating an optical path of first light in a light guide optical system in an inspection apparatus according to a thirteenth embodiment.

An inspection apparatus according to a thirteenth embodiment is a modified example of the seventh embodiment and is different from that according to the seventh embodiment in that a plurality of galvanomirrors (galvanomirrors 56A and 56B) are arranged in a stage previous to an optical mirror 71 configured as an optical path switching element M in a light guide optical system 4M as illustrated in FIGS. 27 and 28.

More specifically, in the light guide optical system 4M, the optical mirror 71 is retracted from an optical path to transmit first light. The optical path of the first light is substantially the same as that of the seventh embodiment as illustrated in FIG. 27. Polarized components orthogonal to each other in the first light are output to a light sensor (i) 7a and a light sensor (ii) 7b of a first light sensor 7A of a light detection unit 7 by a polarization control element K1 and a polarization control element K2 and differential detection is performed. In the light guide optical system 4M, the optical mirror 71 is advanced to the optical path to reflect second light. The optical path of the second light is substantially the same as that of the seventh embodiment as illustrated in FIG. 28. The second light which reciprocates in a λ/4 wavelength plate 55 and becomes linearly polarized light whose polarization plane is rotated by 90° is output to a second light sensor 7B of the light detection unit 7.

Also, in such a form, because the optical path switching element M is configured only for advancing and retracting the optical mirror 71, it is possible to accurately perform both detection of the presence/absence of abnormality of a measurement target D and the acquisition of a pattern while avoiding complication of a configuration.

In the present embodiment, differential detection between one polarized component of the first light and the other polarized component of the first light becomes possible in the light detection unit 7. Therefore, even when an SN ratio of a light source is relatively low, it is possible to accurately detect the presence/absence of abnormality of the measurement target D. Also, the optical path switching element M may include a dichroic mirror or a half mirror. In this case, because a physical operation is unnecessary, the optical path switching element M can be more simply configured.

Fourteenth Embodiment

An inspection apparatus according to a fourteenth embodiment is a modified example of the eighth embodiment and is different from that of the eighth embodiment in that a plurality of galvanomirrors (galvanomirrors 56A and 56B) are provided in a stage previous to the optical mirror 71 configured as an optical path switching element M in a light guide optical system 4N as illustrated in FIGS. 29 and 30.

Also, in such a form, it is possible to accurately perform both detection of the presence/absence of abnormality of a measurement target D and acquisition of a pattern while avoiding complication of the configuration by an optical path switching element M. Such a form is useful when an SN ratio of a light source can be sufficiently secured. In such a form, it is possible to reduce the number of optical elements used for the light guide optical system 4N and simplify a configuration.

Although embodiments of the present invention have been described above, the present invention is not limited to the above-described embodiments. For example, instead of the Faraday rotator used in the above-described embodiment, a variable polarization rotator (a variable rotator) or the like may be used.

REFERENCE SIGNS LIST

1 Inspection apparatus
3 Light output unit
4A to 4N Light guide optical system
6 Magneto-optical crystal
7 Light detection unit
7A First light sensor
7B Second light sensor
32, 82 Dichroic mirror
34 Faraday rotator (optical path switching element)
35 λ/4 wavelength plate (optical path switching element)
56 Galvanomirror (optical path switching element)
61 Dichroic mirror (optical path switching element)
71 Optical mirror (optical path switching element)
D Measurement target
K (K1, K2) Polarization control element
L (L1, L2) Polarization control element
M Optical path switching element

The invention claimed is:

1. An inspection apparatus for inspecting a measurement target, the inspection apparatus comprising:
a light output unit comprising a first light source configured to output first light having a first wavelength and a second light source configured to output second light having a second wavelength different from the first wavelength;
a magneto-optical crystal having a reflection surface configured to reflect the first light, the reflection surface being arranged facing the measurement target;
a light detection unit comprising a first light sensor configured to detect the first light and a second light sensor configured to detect the second light; and
a light guide optical system comprising a plurality of optical elements and configured to guide the first light and the second light toward the magneto-optical crystal and the measurement target and guide the first light reflected by the magneto-optical crystal and the second light reflected by the measurement target toward the light detection unit,
wherein the light guide optical system comprises an optical path switching element configured to perform switching between optical paths of the plurality of optical elements so that the first light and the second light are selectively incident on the light detection unit,
wherein the light guide optical system comprises a polarization control element configured to guide one polarized component of the first light to the light detection unit,
wherein the optical path switching element comprises a galvanomirror configured to switch between the optical paths by adding a first offset or a second offset to a central angle of a scanning range of the galvanomirror,
wherein the galvanomirror is configured to scan the first light to the magneto-optical crystal, and
wherein the galvanomirror is configured to add the first offset if the first light is output from the light output unit, and add the second offset if the second light is output from the light output unit.

2. The inspection apparatus according to claim 1, wherein the light guide optical system further comprises a polarization control element configured to guide the other polarized component of the first light to the light detection unit.

3. The inspection apparatus according to claim 1, wherein the light guide optical system comprises a polarization control element configured to guide one polarized component of the second light to the light detection unit.

4. The inspection apparatus according to claim 1, wherein the optical path switching element comprises a Faraday rotator and a wavelength plate.

5. The inspection apparatus according to claim 4, wherein the light guide optical system is configured to comprise a dichroic mirror, and
wherein the dichroic mirror is arranged in a stage previous to the polarization control element.

6. The inspection apparatus according to claim 1, wherein the optical path switching element comprises a dichroic mirror.

7. The inspection apparatus according to claim 1, wherein the optical path switching element comprises an optical mirror.

8. The inspection apparatus according to claim 1, wherein the measurement target is a semiconductor device.

9. The inspection apparatus according to claim 1, wherein the first wavelength is shorter than the second wavelength.

10. An inspection method of inspecting a measurement target by using a magneto-optical crystal arranged facing the measurement target, the inspection method comprising the step of:

guiding first light having a first wavelength and second light having a second wavelength different from the first wavelength toward the magneto-optical crystal and the measurement target through a light guide optical system and detecting the first light and the second light reflected by the magneto-optical crystal or the measurement target, wherein the step comprises the steps of:

outputting the first light from a first light source of a light output unit and detecting the first light in a first light sensor of a light detection unit via the light guide optical system;

selectively performing switching between optical paths of the light guide optical system so that the second light is incident on the light detection unit; and outputting the second light from a second light source of the light output unit and detecting the second light in a second light sensor of the light detection unit via the light guide optical system, wherein selectively performing switching between optical paths of the light guide optical system includes adding a first offset or a second offset to a central angle ofa scanninn rane of a galvanomirror.

* * * * *